(12) United States Patent
Weiner et al.

(10) Patent No.: US 10,226,528 B2
(45) Date of Patent: Mar. 12, 2019

(54) VACCINES WITH BIOMOLECULAR ADJUVANTS

(71) Applicants: David B. Weiner, Merion, PA (US); Karuppiah Muthumani, Cherry Hill, NJ (US)

(72) Inventors: David B. Weiner, Merion, PA (US); Karuppiah Muthumani, Cherry Hill, NJ (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 14/774,428

(22) PCT Filed: Mar. 14, 2014

(86) PCT No.: PCT/US2014/029679
§ 371 (c)(1),
(2) Date: Sep. 10, 2015

(87) PCT Pub. No.: WO2014/145038
PCT Pub. Date: Sep. 18, 2014

(65) Prior Publication Data
US 2016/0067334 A1 Mar. 10, 2016

Related U.S. Application Data

(60) Provisional application No. 61/800,328, filed on Mar. 15, 2013.

(51) Int. Cl.
| | |
|---|---|
| *A61K 39/39* | (2006.01) |
| *A61K 39/12* | (2006.01) |
| *A61K 39/21* | (2006.01) |
| *C07K 14/52* | (2006.01) |
| *C12N 7/00* | (2006.01) |
| *A61K 41/00* | (2006.01) |
| *C07K 14/47* | (2006.01) |
| *A61K 39/00* | (2006.01) |

(52) U.S. Cl.
CPC .............. *A61K 39/39* (2013.01); *A61K 39/12* (2013.01); *A61K 39/21* (2013.01); *A61K 41/0047* (2013.01); *C07K 14/4702* (2013.01); *C07K 14/52* (2013.01); *C12N 7/00* (2013.01); *A61K 2039/53* (2013.01); *A61K 2039/55516* (2013.01); *A61K 2039/55522* (2013.01); *C12N 2740/16034* (2013.01); *C12N 2740/16134* (2013.01); *C12N 2740/16171* (2013.01); *C12N 2740/16234* (2013.01); *C12N 2740/16271* (2013.01)

(58) Field of Classification Search
None
See application file for complete search history.

(56) References Cited

U.S. PATENT DOCUMENTS

| | | | |
|---|---|---|---|
| 8,017,398 B2 * | 9/2011 | Lee | C12N 15/1055 435/252.3 |
| 8,227,193 B2 | 7/2012 | Karin et al. | |
| 2007/0104686 A1 | 5/2007 | Weiner et al. | |
| 2007/0218086 A1 | 9/2007 | Tiollier | |
| 2007/0298021 A1 | 12/2007 | Von Stein et al. | |
| 2007/0298051 A1 | 12/2007 | Barouch et al. | |
| 2008/0220014 A1 | 9/2008 | Pau et al. | |
| 2009/0069256 A1 * | 3/2009 | Smith | C07H 21/02 514/44 R |
| 2012/0148622 A1 | 6/2012 | tenOever et al. | |

FOREIGN PATENT DOCUMENTS

| | | |
|---|---|---|
| CN | 102949733 A | 3/2013 |
| JP | H11-155581 | 6/1999 |
| WO | 2004107618 A2 | 12/2004 |
| WO | 2005080568 A1 | 9/2005 |
| WO | 2007120368 A2 | 10/2007 |
| WO | 2010068680 A1 | 6/2010 |
| WO | 2012040266 A2 | 3/2012 |

OTHER PUBLICATIONS

GenBank: ACI43214.1. HPV-16 E6/E7 fusion protein [synthetic construct]. Jan. 14, 2009.*
GenBank: BC003818.1. Mus musculus v-rel reticuloendotheliosis viral oncogene homolog A (avian), mRNA (cDNA clone MGC:6177 IMAGE:3489295), complete cds. Dated Dec. 2, 2006.*
GenBank: AAF61242.1. T-cell-specific T-box transcription factor T-bet [Mus musculus]. Dated Apr. 6, 2000.*
GenBank: AF241242.1 Mus musculus T-cell-specific T-box transcription factor T-bet mRNA, complete cds. Dated Apr. 6, 2000.*
Xu et al. Recombinant DNA vaccine of the early secreted antigen ESAT-6 by Mycobacterium tuberculosis and Flt3 ligand enhanced the cell-mediated immunity in mice. Vaccine 26 (2008) 4519-4525.*
Kalams et al. Safety and Comparative Immunogenicity of an HIV-1 DNA Vaccine in Combination with Plasmid Interleukin 12 and Impact of Intramuscular Electroporation for Delivery. The Journal of Infectious Diseases 2013;208:818-29.*
GenBank: AAA90951.1 Flt3 ligand [Mus musculus]. Dated Feb. 28, 1996.*
Bozzacco et al. "HIV gag protein is efficiently cross-presented when targeted with an antibody towards the DEC-205 receptor in FL T3 ligand-mobilized murine dendritic cells". Eur J Immunol. 40(1): pp. 36-46 (Jan. 1, 2010).
Kanagavelu et al., "Soluble multi-trimeric TNF superfamily ligand adjuvants enhance immune responses to a HIV-1 Gag DNA vaccine". Vaccine, vol. 30, No. 4:691-702 (2012).

(Continued)

*Primary Examiner* — Nianxiang Zou
(74) *Attorney, Agent, or Firm* — Riverside Law LLP

(57) ABSTRACT

Disclosed herein is a vaccine comprising an antigen and one or more bimolecular adjuvant. Also disclosed herein are methods for increasing an immune response in a subject. The methods may comprise administering the vaccine to the subject in need thereof.

19 Claims, 20 Drawing Sheets
Specification includes a Sequence Listing.

(56) References Cited

OTHER PUBLICATIONS

Kayamuro et al., "Identification of New Candidates as Mucosal Vaccine Adjuvant in TNF Family Cytokines". Advances in Experimental Medicine and Biology 2011, vol. 691: pp. 299-304 (2011).

Stone et al., "Multimeric Soluble CD40 Ligand and GITR Ligand as Adjuvants for Human Immunodeficiency Virus DNA Vaccines". Journal of Virology, vol. 80(4):1762-1772 (2006).

Winkles, "The TWEAK-Fn14 cytokine-receptor axis: discovery, biology and therapeutic targeting". Nature Reviews, vol. 7, No. 5:411-425 (May 1, 2008).

Nolan et al., "DNA Binding and IKB Inhibition of the Cloned p65 Subunit of NF-KappaB, a rel-Related Polypeptide", Cell, vol. 64, No. 5: pp. 961-969 (Mar. 8, 1991).

Vallabhapurapu et al., "Regulation and function of NF-kappaB transcription factors in the immune system", Annual Review of Immunology 2009, vol. 27, pp. 693-733 (2009).

Castaldello et al., "Interferon Regulatory Factor-1 Acts as a Powerful Adjuvant in tat DNA Based Vaccination", Journal of Cellular Physiology, vol. 224, No. 3, pp. 702-709 (Apr. 28, 2010).

Shedlock et al., "Co-Administration of Molecular Adjuvants Expressing NF-Kappa B Subunit p65/RelA or Type-1 Transactivator T-bet Enhance Antigen Specific DNA Vaccine-Induced Immunity", Vaccines, vol. 2, No. 2, pp. 196-215 (2014).

Hu et al., "T-bet acts as a powerful adjuvant in Ag85B DNA-based vaccination against tuberculosis", Molecular Medicine Reports, vol. 6, pp. 139-144 (2012).

Kutzler et al., "DNA vaccines: ready for prime time?," Nature Reviews, Genetics, Oct. 2008, 9:776-788, XP-002621067.

GenBank: AAB59424.1, "Ig heavy chain epsilon-1 (V-D-J region) [*Homo sapiens*]," published Feb. 11, 2002.

\* cited by examiner

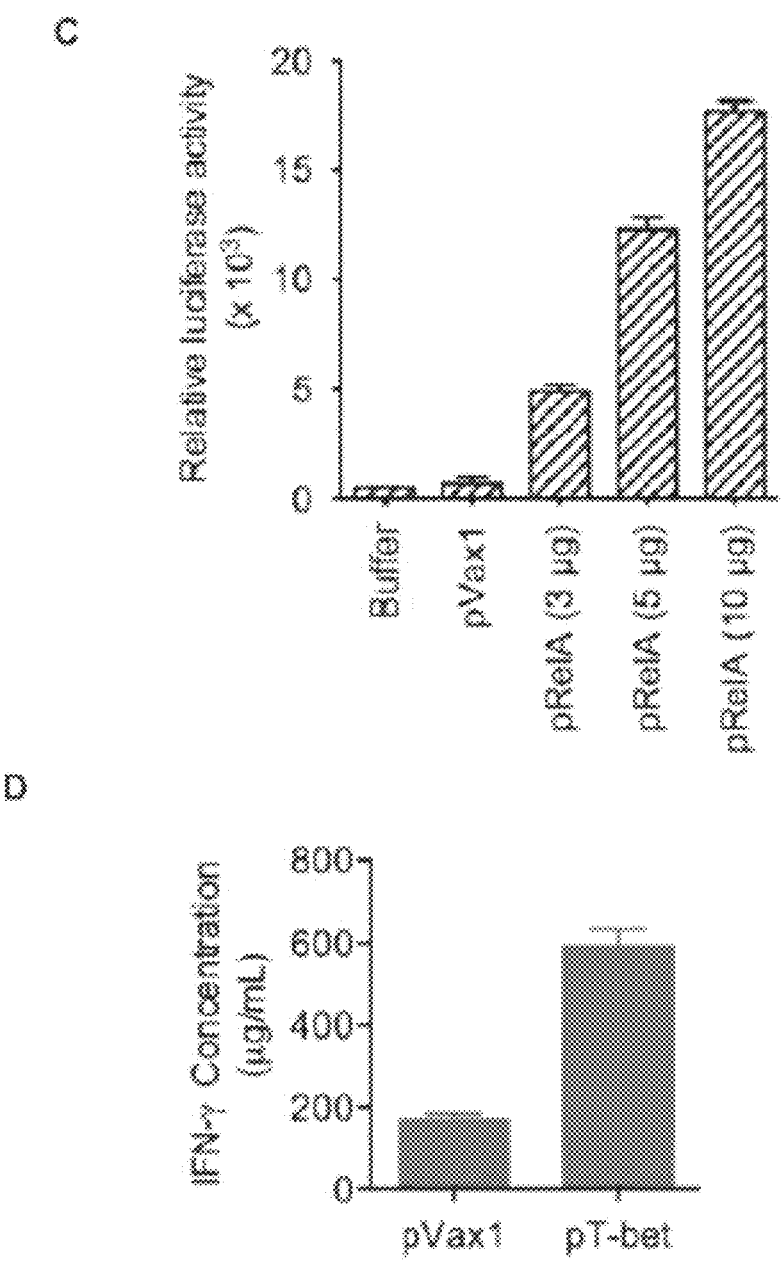
FIG. 1 (con't)

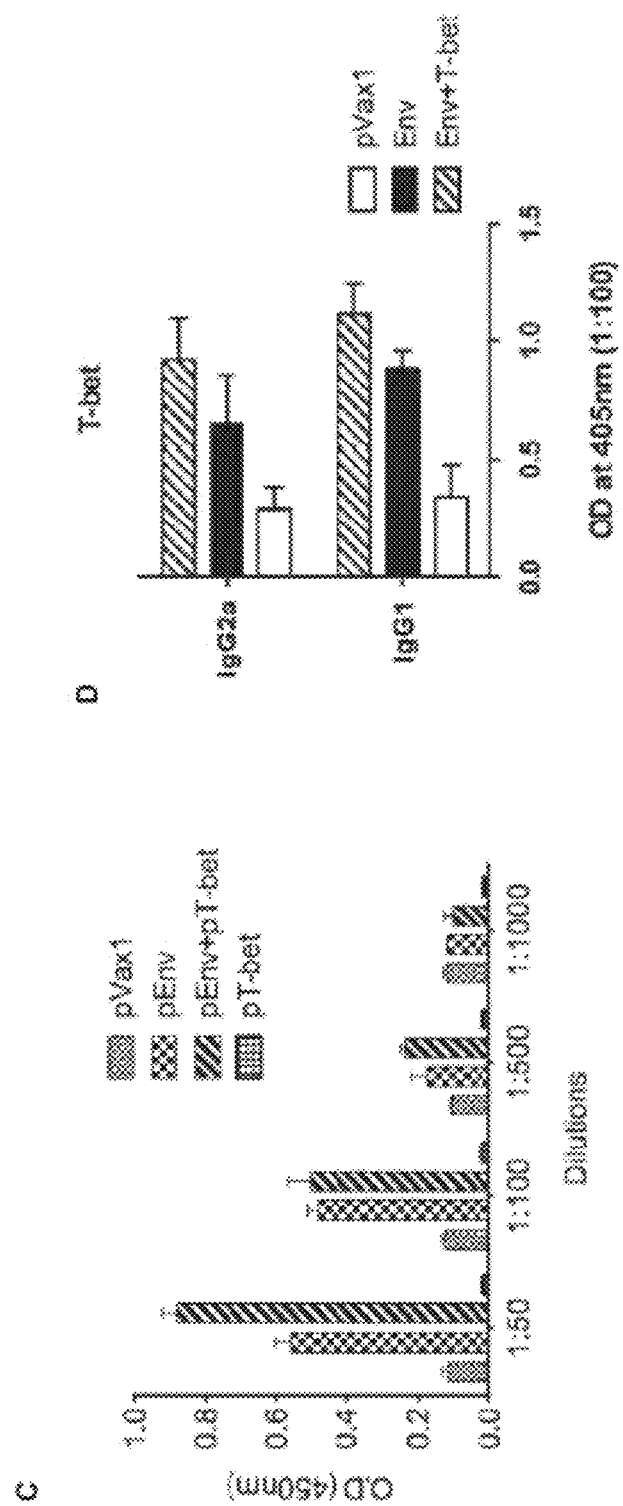
FIG. 8 (con't)

VACCINES WITH BIOMOLECULAR ADJUVANTS

CROSS-REFERENCE TO RELATED APPLICATIONS

This application is the U.S. national stage application filed under 35 U.S.C. § 371 claiming benefit to International Patent Application No. PCT/US14/029679, filed Mar. 14, 2014, which is entitled to priority under 35 U.S.C. § 119(e) to U.S. Provisional Application Nos. 61/800,328, filed Mar. 15, 2013, each of which is hereby incorporated by reference in its entirety.

STATEMENT OF GOVERNMENT INTEREST

This invention was made with government support under contract number 5-P30-AI-045008-13 awarded by the National Institutes of Health. The government has certain rights in the invention.

TECHNICAL FIELD

The present invention relates to vaccines comprising an antigen and either one or more bimolecular adjuvants, and methods of administering such vaccines.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant with the vaccine. Adjuvants come in many different forms such as aluminum salts, oil, emulsions, sterile constituents of bacteria and/or pathogens.

DNA vaccine induced immunity can be enhanced by co-delivery of synthetic gene encoding molecular adjuvants as well. Many of these adjuvants have included cytokines and chemokines that have been demonstrated to enhance vaccine-induced immunity by increasing the magnitude or type of immune response and/or protective efficacy. Through the use of molecular adjuvants, immune responses can be highly customizable and functionally tailored for optimal efficacy against pathogen specific (i.e., infectious agent) or non-pathogen (i.e., cancer) antigens.

In addition to these molecular adjuvants, vaccines are also administered in many different ways (e.g., injection, orally, etc.) into many different tissues (e.g., intramuscular, intradermal etc.). Not all delivery methods, are equal and require greater compliance within a population of individuals while other delivery methods may affect the immunogenicity and/or safety of the vaccine. There remains a need in the art for the development of safe and more effective adjuvants, and in particular, molecular adjuvants combined with particular delivery methods in order to provide a customizable and functionally tailored vaccination for optimal efficacy against pathogenic and non-pathogenic antigens.

SUMMARY OF THE INVENTION

The present invention is directed to a vaccine comprising an antigen, and one or more adjuvants selected from the group consisting of: Rel-A, T-bet, Eomes, FLT3L, TWEAK, GITRL and STING. The antigen of the vaccine is encoded by a first nucleic acid and the adjuvant is encoded by a second nucleic acid. The first and second nucleic acids of the vaccine may be expressed from an expression vector. The antigen of the vaccine is selected from a group consisting of a human papilloma virus (HPV) antigen, an HIV antigen, an influenza antigen, a *Plasmodium falciparum* antigen, or fragment thereof. The HPV antigen can be selected from the group consisting of HPV16 E6 antigen, an HPV16 E7 antigen and combination thereof. The HIV antigen can be selected from the group consisting of Env A, Env B, Env C, Env D, B Nef-Rev, Gag, and any combination thereof. The influenza antigen is selected from the group consisting of H1 HA, H2 HA, H3 HA, H5 HA, BHA antigen and combination thereof. The *Plasmodium falciparum* antigen may include a circumsporozoite (CS) antigen. The vaccine can further comprise a pharmaceutically acceptable excipient.

The present invention is further directed to a method for increasing an immune response in a subject, the method comprising administering the vaccine of claim 1 to the subject in need thereof, wherein administering the vaccine includes at least one of intramuscular administration and intradermal administration. The vaccine can also be administered through electroporation. The method increases immune response occurs in at least one of a skin tissue and a muscle tissue of the subject, and increase the immune response in the subject by about 50% to about 150%, or between 90% to 130%, or 105%. The method of vaccination the adjuvant may increase the immune response in the subject in need thereof by at least about 0.5 fold, 1.0-fold, 1.5 fold, 2.0 fold, 2.5 fold, 3.0 fold, 3.5 fold, or 4.0 fold.

Figure 3:
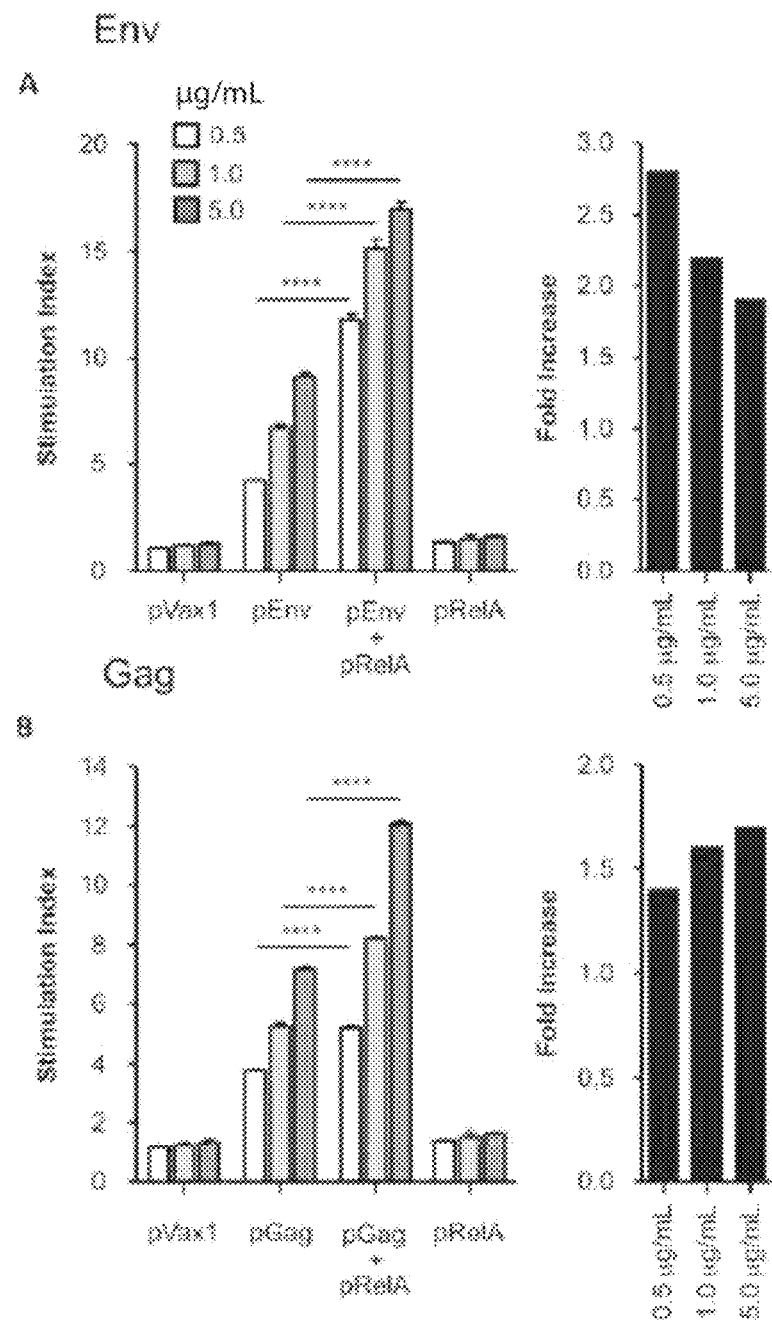

FIG. 3 shows increased T-cell proliferative potential following DNA vaccination plus co-administration of pRelA. Proliferative responses were measured 7 days following the third vaccination with either pEnv or pGag alone, pEnv or pGag with pRelA molecular adjuvant, or empty vector control pVax1 alone. Splenocytes were incubated with recombinant HIV-1 Env (A) or Gag (B) at various concentrations: 0.5 (white bars), 1.0 (light gray bars), and 5.0 (dark gray bars) and subsequently pulsed with tritiated (3H)-thymidine for 24 h. Incorporated thymidine was expressed as a stimulation index (SI) calculated by dividing the mean cpm (counts per minute) of Ag-stimulated wells by the mean cpm of non-stimulated wells. Fold increase in SI for pRelA-adjuvanted mice are displayed for each concentration of Env (A, right panel) or Gag (B, right panel). Samples were tested in triplicate. Error bars represent the SEM, and statistically significant values are provided for the indicated group comparison shown in the graphs. ****p<0.0001.

Figure 4:
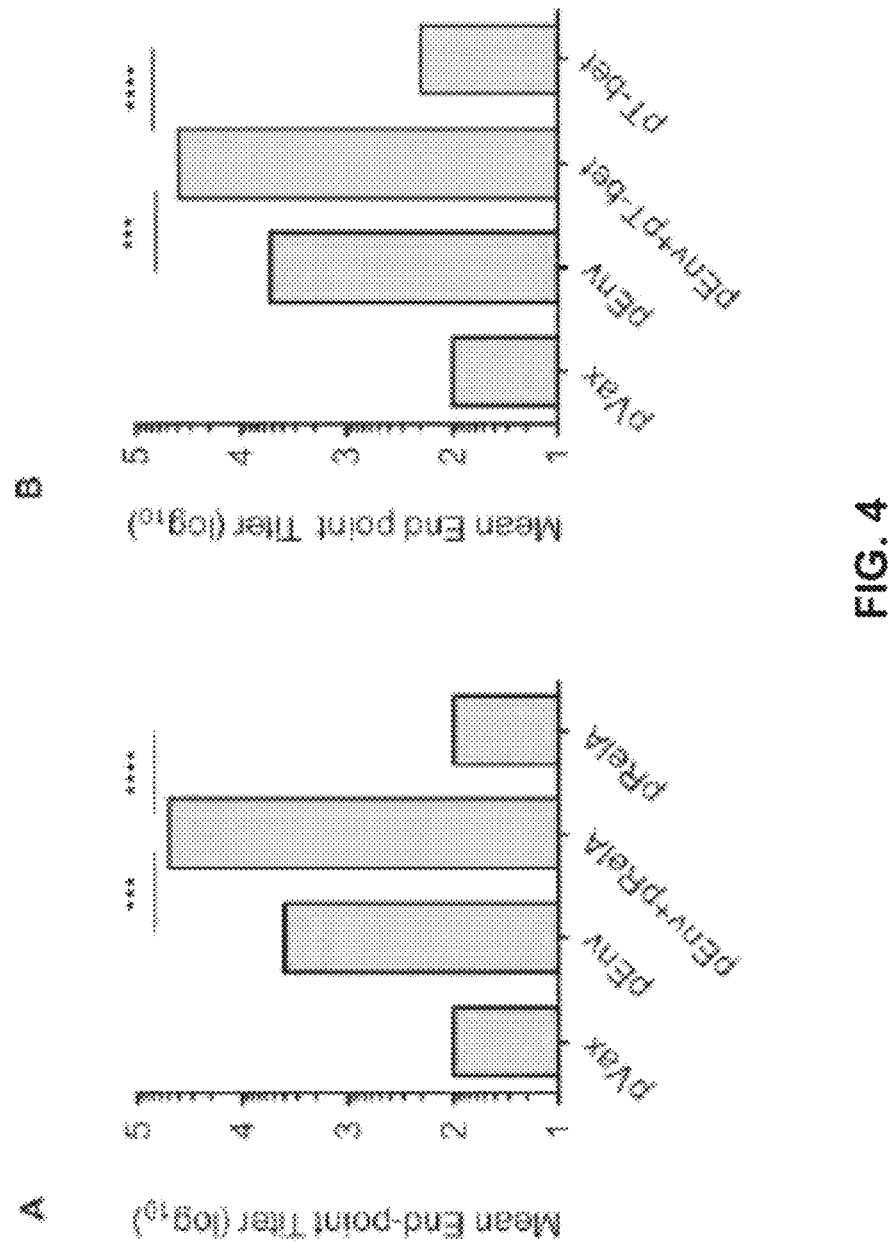

FIG. 4 shows improved B-cell responses with pEnv vaccination and co-administered transcriptional molecular adjuvant. B-cell/antibody responses were assessed in the sera of vaccinated mice (n=4/group) 7 days following the third immunization with pEnv alone, pEnv in combination with either pRelA or pTbet, each of the molecular adjuvants alone, or with empty vector control plasmid (pVax1). Anti-Env p120 antibody-binding titers were determined by ELISA. Data are presented as the mean endpoint titers. Statistically significant values are indicated; *p<0.001 (comparison between pEnv alone and pEnv+pRelA or pEnv+pT-bet) and **p<0.0001 (comparison between pRelA alone and pEnv+pRelA or pT-bet alone and pEnv+pT-bet).

Figure 5:
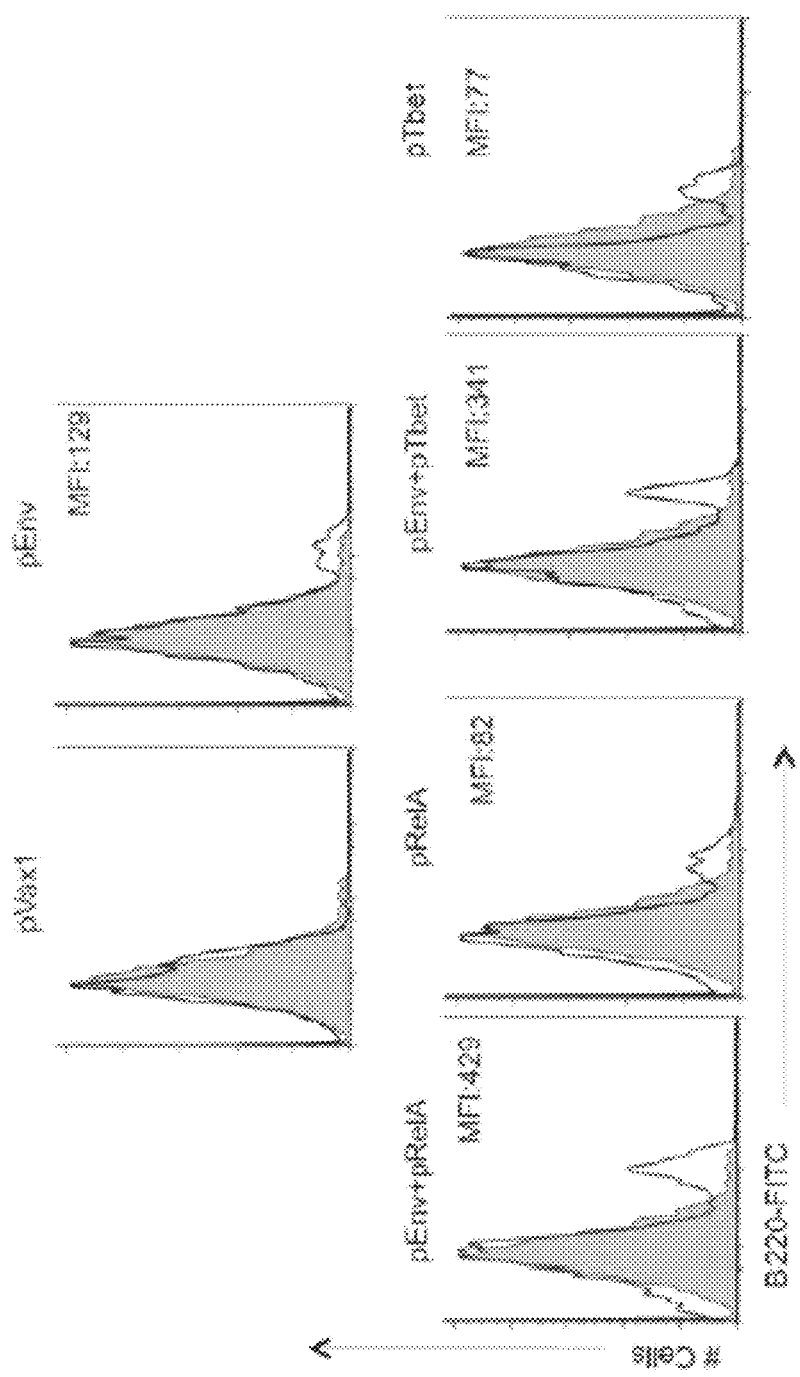

FIG. 5 shows molecular adjuvants induce enhanced population of B-cells at the site of immunization. Cell cultures from the muscle were analyzed by flow cytometry for expression of B220. The isolated cells were incubated in culture media for 3 days and these cells were then stained with DC subsets (CD11c+/CD11b+), B-cells (B220+), T-cells (CD4+ and CD8+ subsets), to distinguish monocytes/dendritic, B-cells and T-cells, respectively. Such differential staining allowed the exclusion of dendritic and T-cells from subsequent analysis of B220 expression. Histograms show the B220+ expression on B-cells exclusively using a specific mAb as well as an isotype-matched, irrelevant mAb as a control. The profile of an isotype-matched irrelevant Ab, used as a control (shaded area) is also indicated in the panels. MFI=mean fluorescent intensity which is proportional to the level of B220 expressing B cells.

Figure 6:
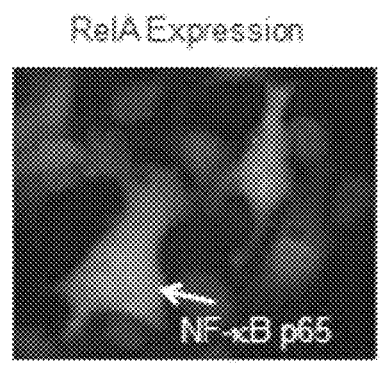

FIG. 6 shows immunostaining of transfected cells for RelA protein.

Figure 7:
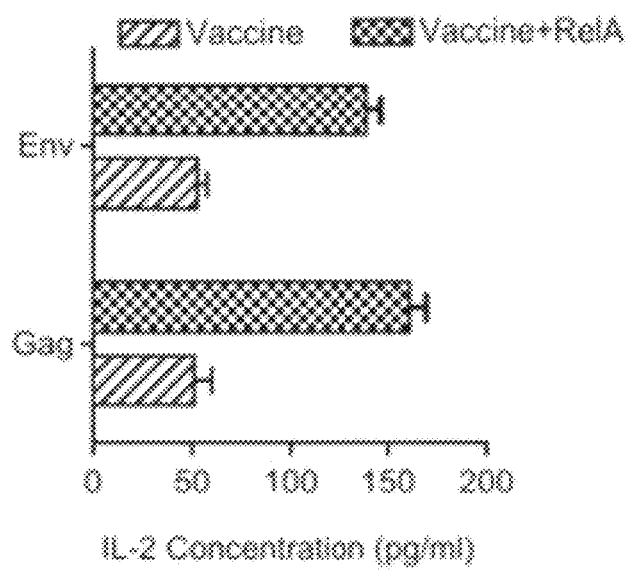

FIG. 7 shows a graph plotting interleukin-2 (IL-2) concentration vs. antigen.

Figure 8:
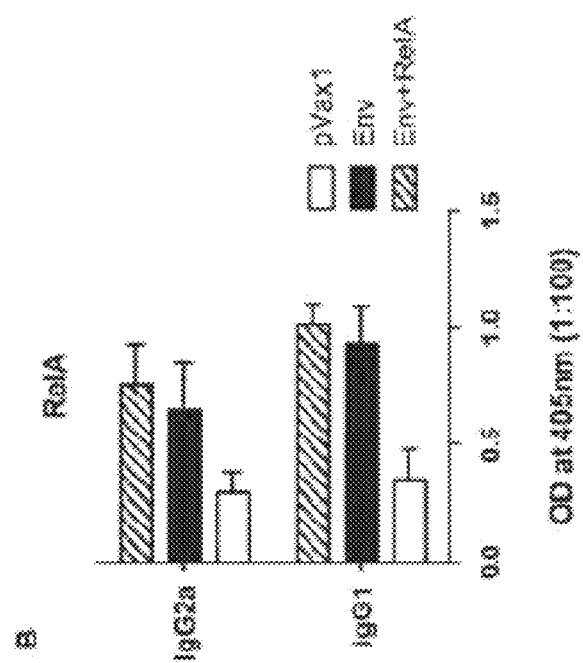
Figure 8:
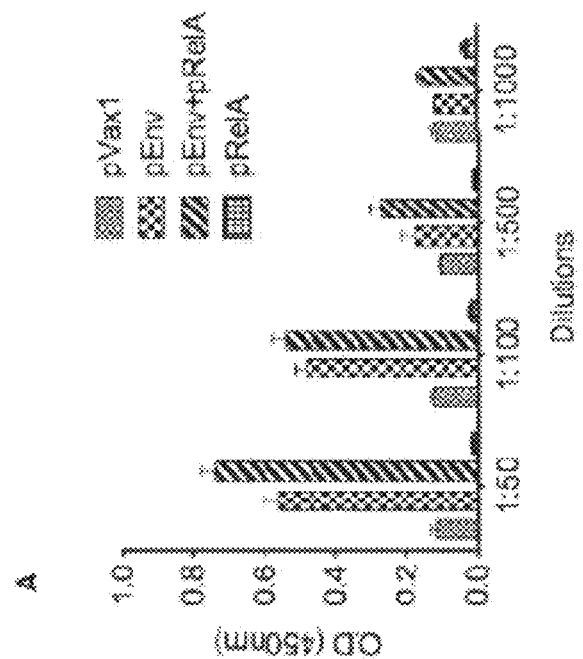

FIG. 8 shows (A,B) total IgG production in RelA adjuvanted mice; and (C, D) total IgG production in T-bet adjuvanted mice.

Figure 9:
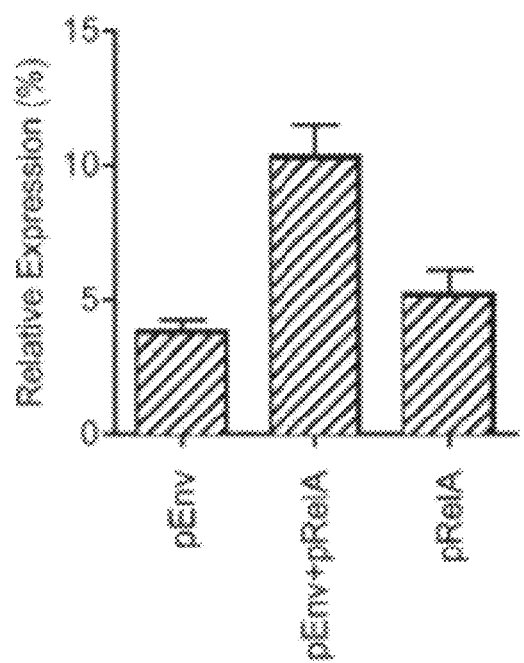

FIG. 9 shows a graph plotting treatment group vs. relative expression (in percent).

Figure 10:
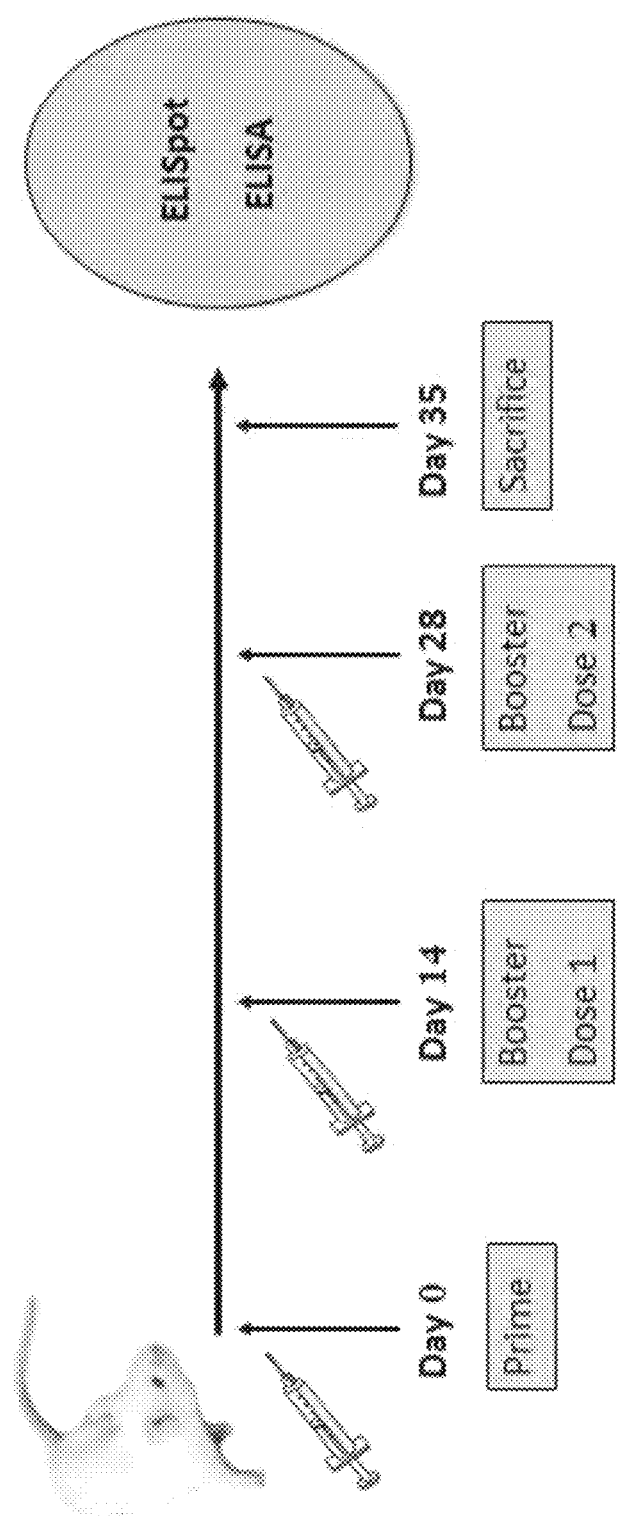

FIG. 10 shows a schematic illustrating an immunization regimen.

Figure 11:
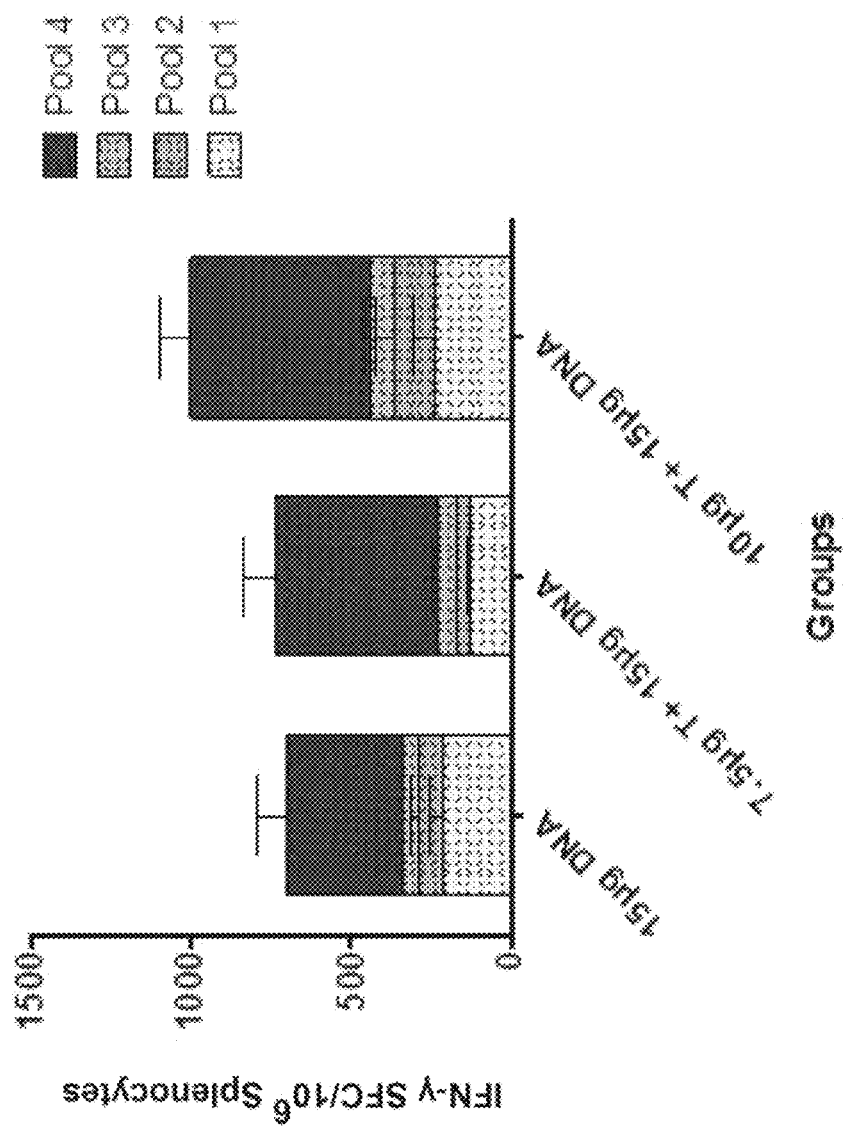

FIG. 11 shows a graph plotting treatment group vs. interferon-gamma (IFN-γ) spot forming colony (SFC) per $10^6$ splenocytes.

Figure 12:
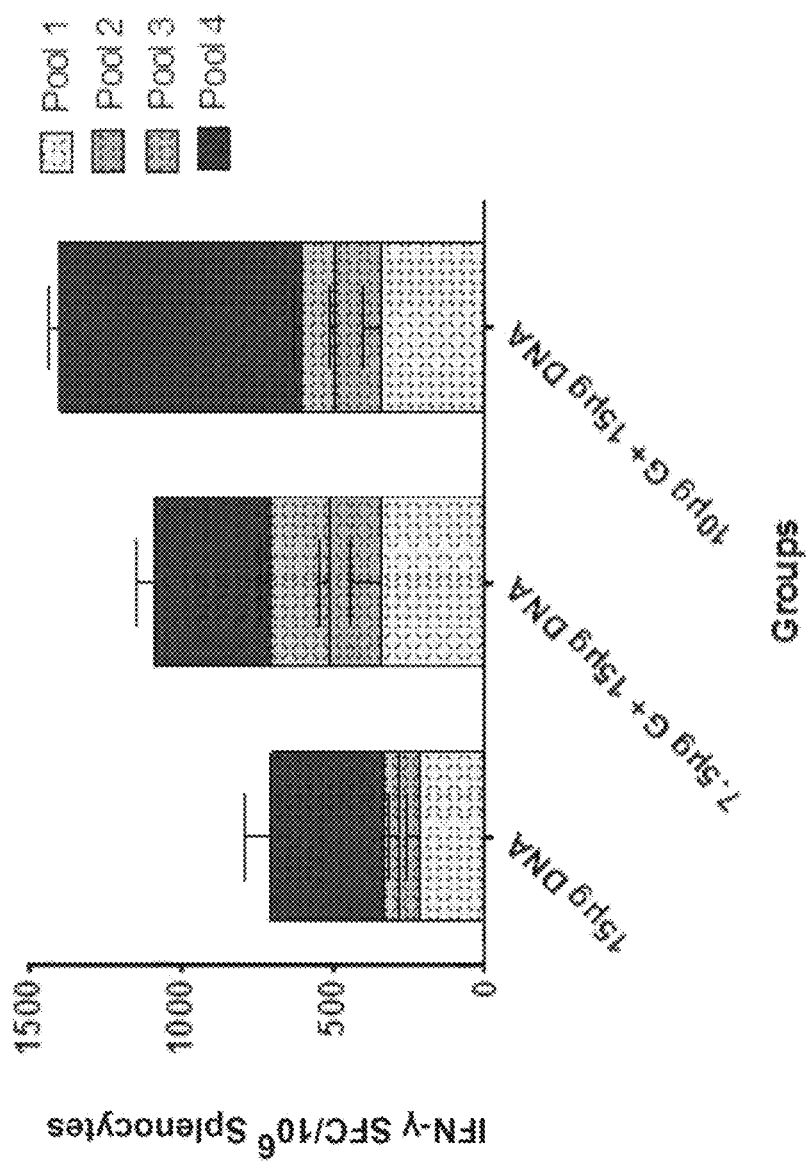

FIG. 12 shows a graph plotting treatment group vs. interferon-gamma (IFN-γ) spot forming colony (SFC) per $10^6$ splenocytes.

Figure 13:
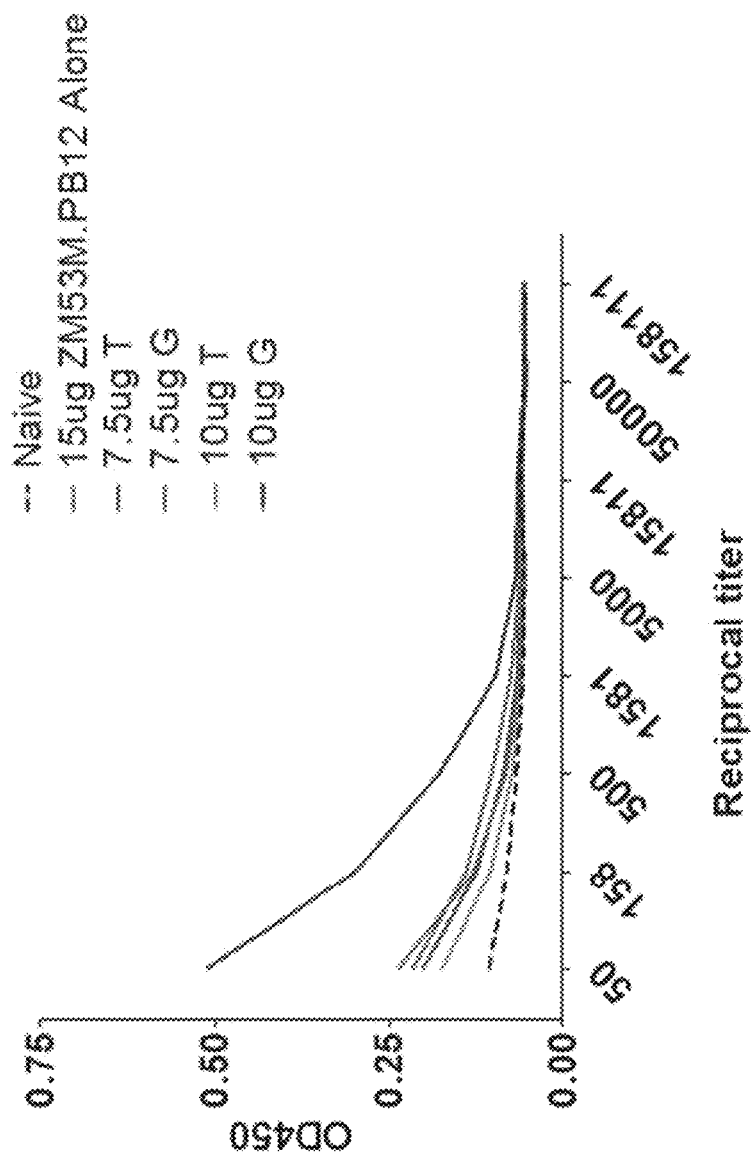

FIG. 13 a graph plotting reciprocal titer vs. OD 450 nm.

Figure 14:
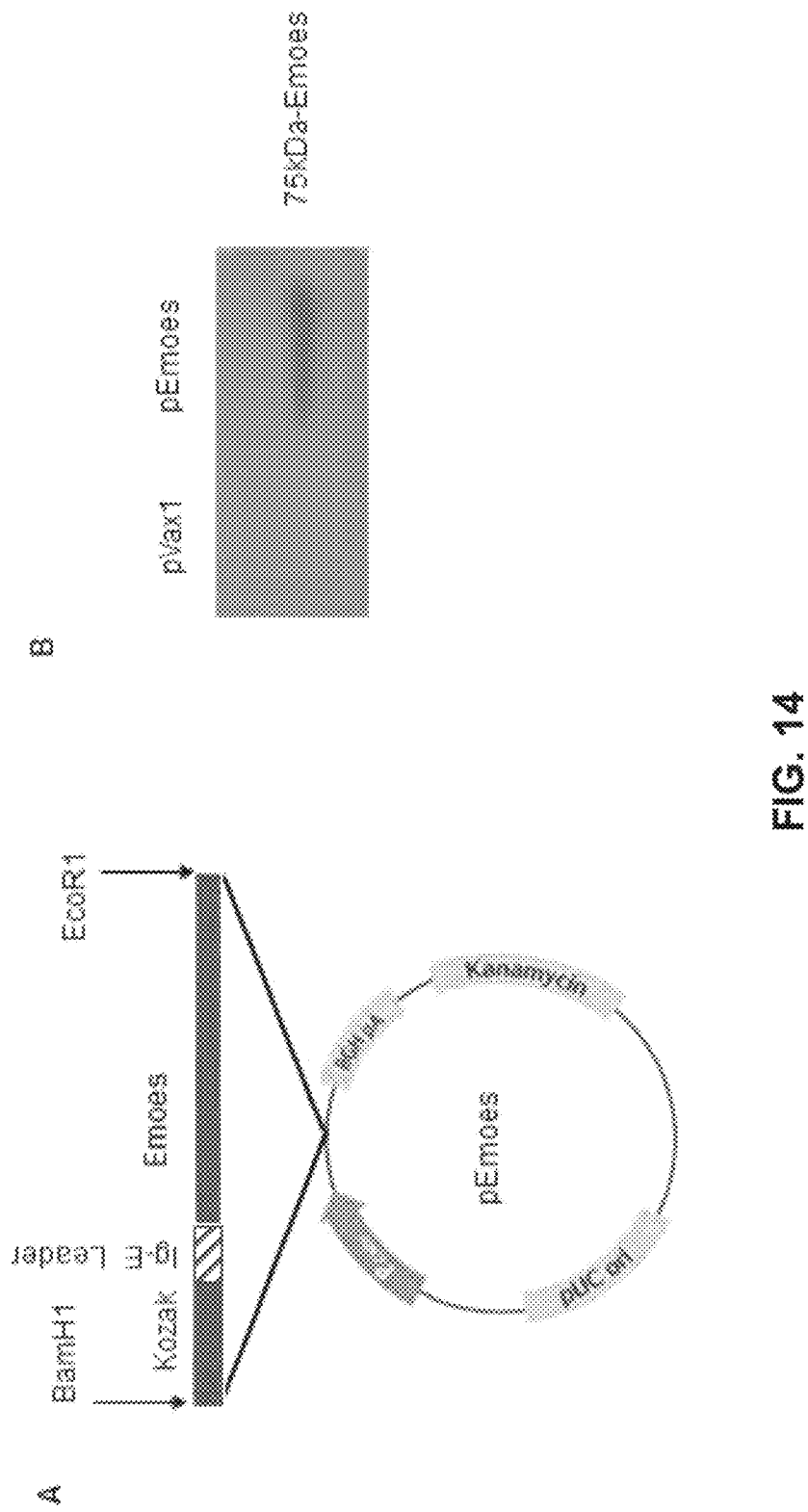

FIG. 14 shows (A) a schematic of the plasmid encoding Eomes; and (B) an image of a western blot.

Figure 15:
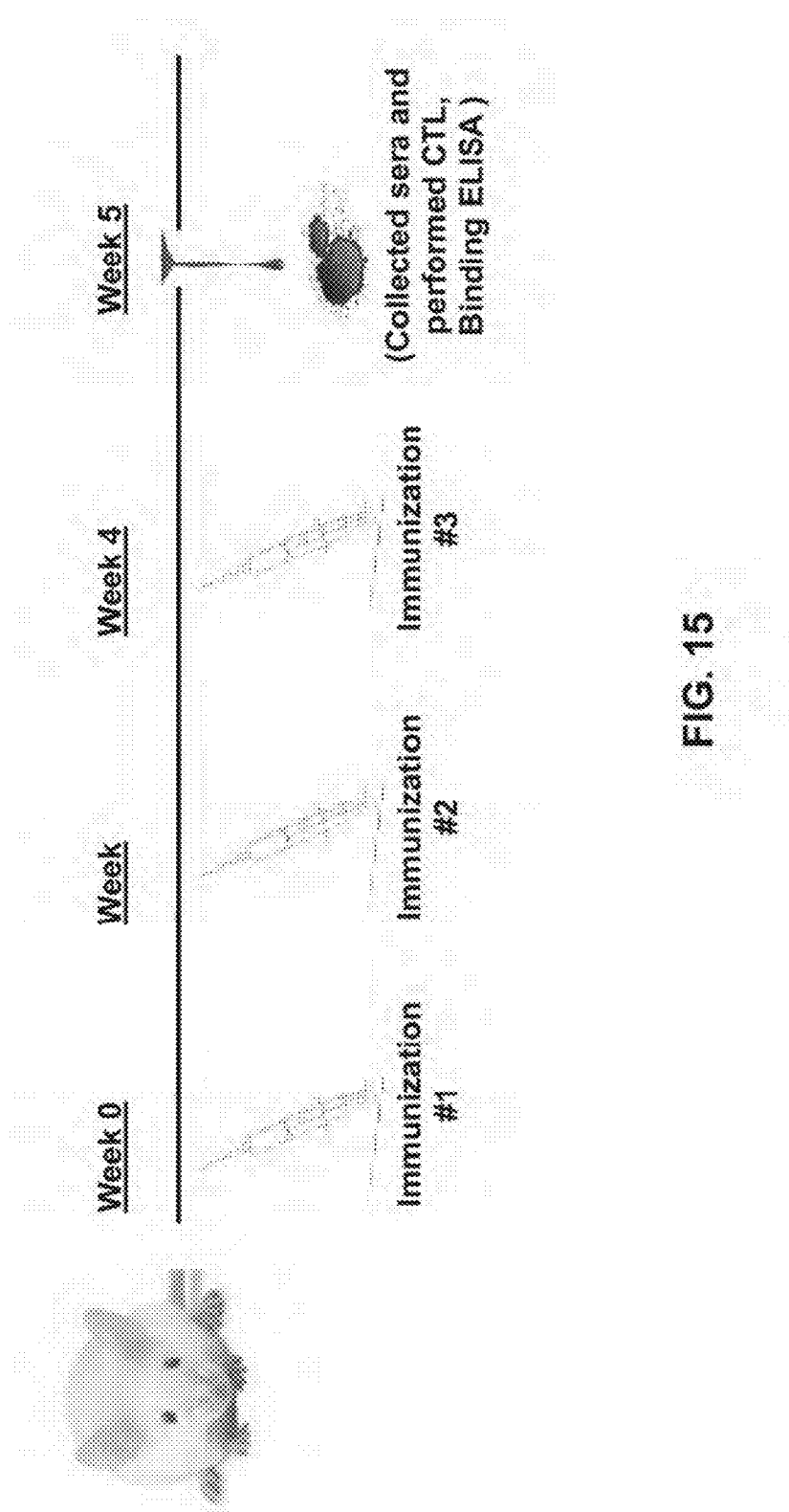

FIG. 15 shows a schematic illustrating an immunization regimen.

Figure 16:
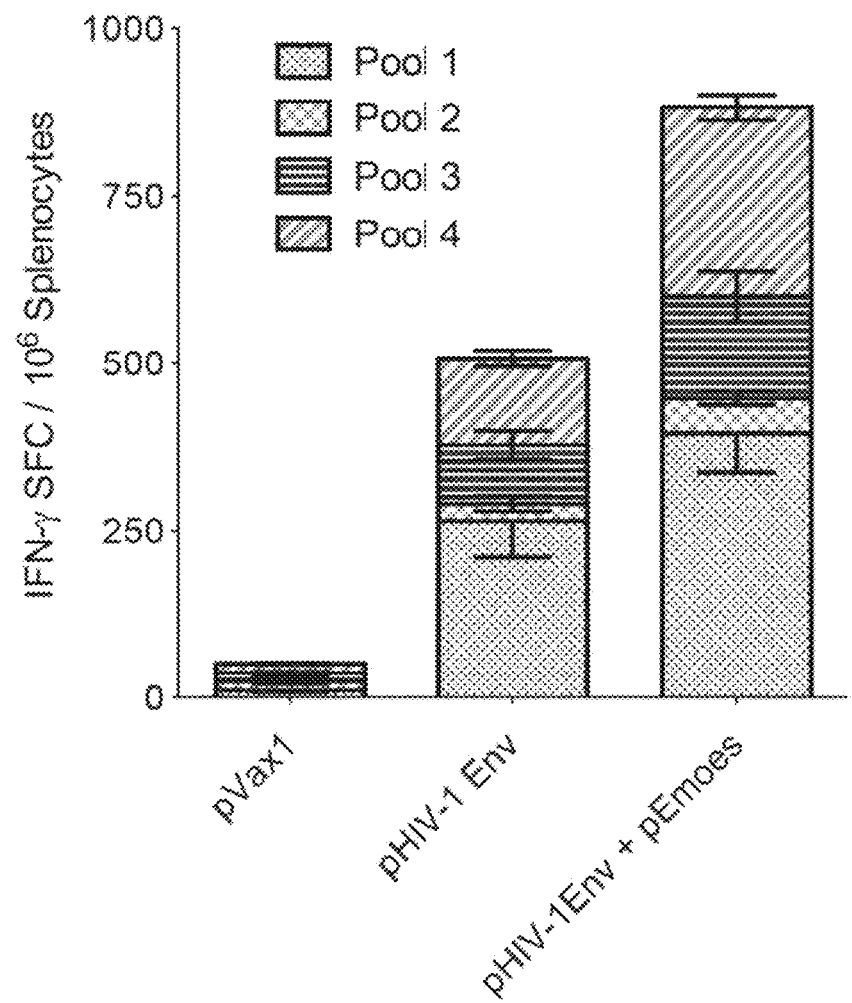

FIG. 16 shows a graph plotting treatment group vs. interferon-gamma (IFN-γ) spot forming colony (SFC) per $10^6$ splenocytes.

Figure 17:
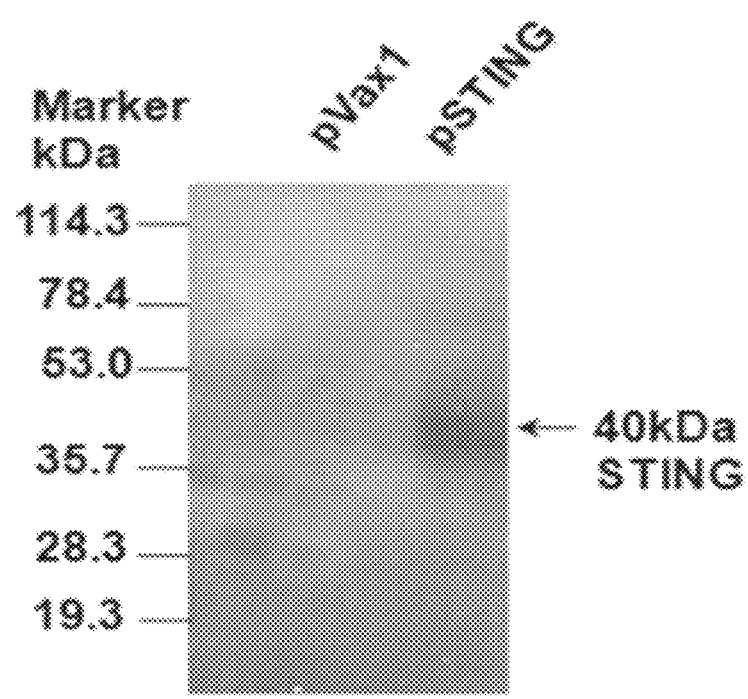

FIG. 17 shows a western blot.

Figure 18:
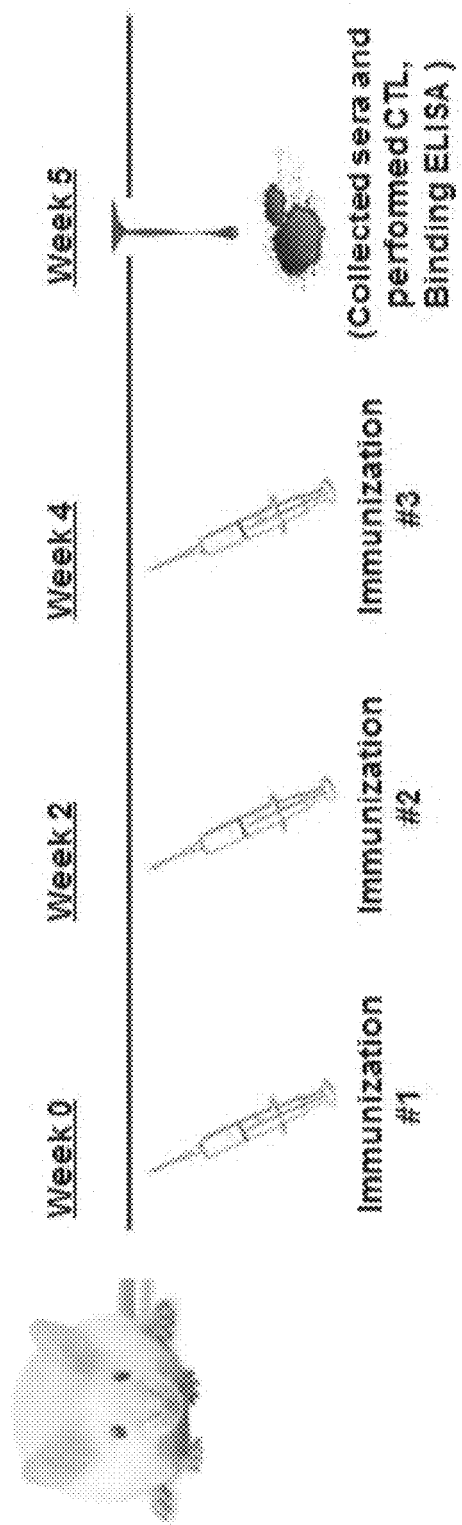

FIG. 18 shows a schematic illustrating an immunization regimen.

Figure 19:
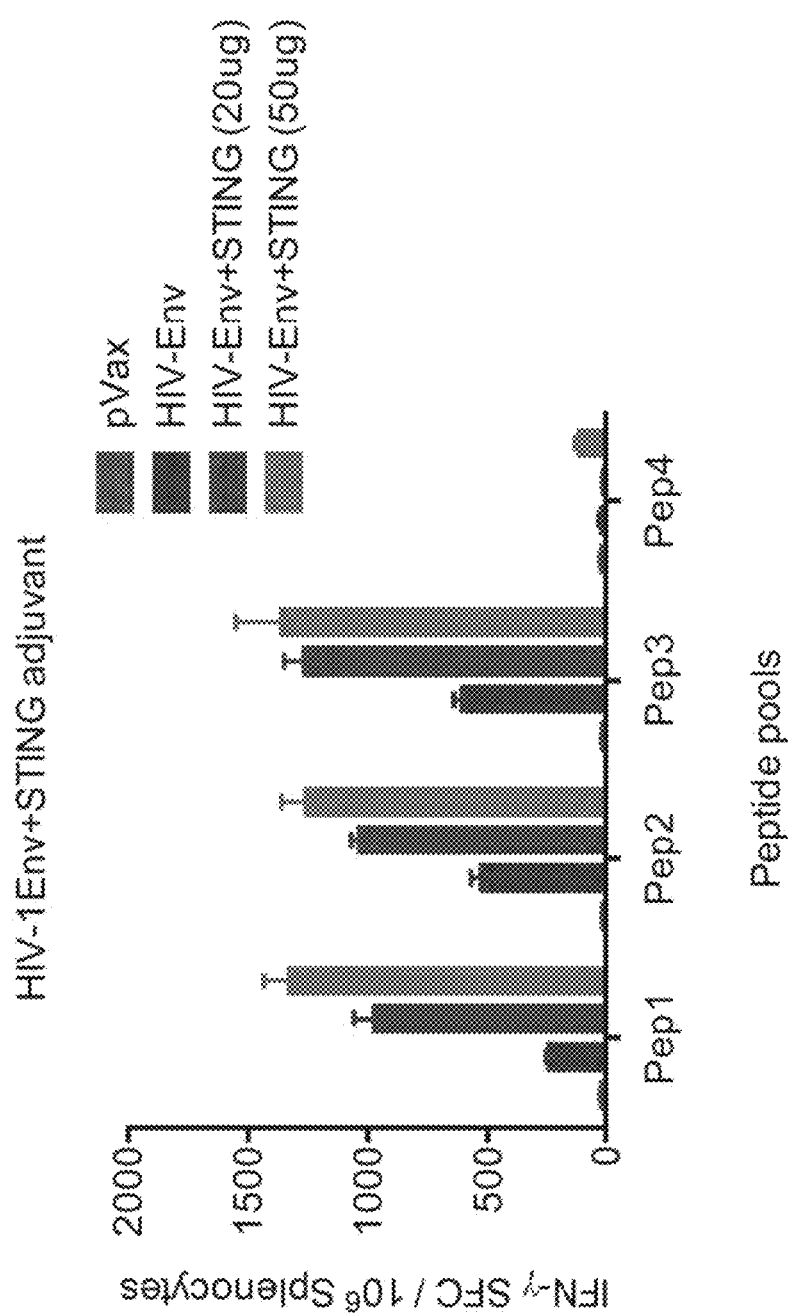

FIG. 19 shows a graph plotting peptide pool vs. interferon-gamma (IFN-γ) spot forming colony (SFC) per $10^6$ splenocytes.

DETAILED DESCRIPTION

The present invention relates to vaccines that can be used to increase an immune response to an antigen in a subject by using as a molecular adjuvant. The molecular adjuvant can be a transcriptional factor, co-stimulatory molecule, chemokine or cytokines. The molecular adjuvant can be Rel-A, T-bet, Eomes, FLT3L, TWEAK, GITRL, STING or combinations thereof.

In some instances, Rel-A, T-bet, Eomes, FLT3L, TWEAK, GITRL or STING can function as a universal adjuvant because a greater immune response is elicited in the subject regardless of the source of the antigen or the route of administration as compared to a vaccine comprising the antigen alone. Rel-A, T-bet, Eomes, FLT3L, TWEAK, GITRL or STING may further augment the immune response of both viral and parasite antigens, for example, human immune deficiency virus (HIV), a human papilloma virus (HPV) antigen and a *Plasmodium falciparum* antigen, respectively. In some instances, Rel-A, T-bet, Eomes, FLT3L, TWEAK, GITRL and STING can further augment the immune response in both muscle and skin tissues as demonstrated by increased interferon-γ (IFN-γ) production.

The vaccines of the present invention can also unexpectedly modify or alter epitope presentation to increase the immune response to the antigen. Such modification can be dependent upon Rel-A, T-bet, Eomes, FLT3L, TWEAK, GITRL and STING. In some instances, Rel-A, T-bet, Eomes, FLT3L, TWEAK, GITRL and STING can direct the immune system to recognize new epitopes in the antigen, in addition to the epitopes recognized by the immune system in the absence of Rel-A, T-bet, Eomes, FLT3L, TWEAK, GITRL and STING. In other instances, Rel-A, T-bet, Eomes, FLT3L, TWEAK, GITRL and STING can remap the landscape of epitope recognition by the immune system to increase the immune response to the antigen across tissues and irrespective of the antigen's identity or source.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccines described herein to enhance the immunogenicity of the antigens.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" or "immunogenic fragment" as used herein means a nucleic acid sequence or a portion thereof that encodes a polypeptide capable of eliciting and/or increasing an immune response in a mammal. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

Fragment or immunogenic fragment as used herein also means a polypeptide sequence or a portion thereof that is capable of eliciting and/or increasing an immune response in a mammal. The fragments can be polypeptide fragments selected from at least one of the various amino acid sequences set forth below. Fragments can comprise at least 10%, at least 20%, at least 30%, at least 40%, at least 50%, at least 60%, at least 70%, at least 80%, at least 90%, or at least 95% of one or more of the proteins set forth below. In some embodiments, fragments can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of at least one of the proteins set forth below.

"Genetic construct" or "construct" as used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs or constructs that contain the necessary regulatory elements operably linked to a coding sequence that encodes a protein such that when present in the cell of the individual, the coding sequence will be expressed.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of an antigen. The immune response can be in the form of a cellular or humoral immune response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein or amino acid sequence set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus of the protein.

"Subject" as used herein can mean a mammal that wants to or is in need of being immunized with the herein described vaccines. The mammal can be a human, chimpanzee, dog, cat, horse, cow, mouse, or rat.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance.

Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Vaccines

Provided herein is a vaccine comprising an antigen and an adjuvant. The vaccine can increase antigen presentation and the overall immune response to the antigen in an individual. The combination of antigen and adjuvant induces the immune system more efficiently than a vaccine comprising the antigen alone. The vaccine can further modify epitope presentation within the antigen to induce a greater immune response to the antigen than a vaccine comprising the antigen alone. The vaccine can further induce an immune response when administered to different issues such as the muscle and the skin.

The vaccine can induce IFN-γ production by at least about 1.5-fold, at least about 2-fold, at least about 3-fold, at least about 4-fold, at least about 5-fold, at least about 8-fold, and at least about 10-fold as compared to a vaccine not including the adjuvant.

The vaccine can increase or boost the cellular and/or humoral immune response to the antigen in a subject as compared to a vaccine without the adjuvant. The vaccine can increase the cellular and/or humoral immune response to the antigen by about 75% to about 200%. Alternatively, the vaccine can increase the cellular and/or humoral immune response to the antigen may be increased by about 90% to about 130% as compared to a vaccine without the adjuvant. The vaccine can increase the cellular and/or humoral immune response to the antigen may be increased by about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without the adjuvant.

The vaccine of the present invention can have features required of effective vaccines such as being safe so the vaccine itself does not cause illness or death; protective again illness resulting from exposure to live pathogens such as viruses or bacteria; induces neutralizing antibody to prevent infection of cells; induces protective T cell against intracellular pathogens; and provides a ease of administration, few side effects, biological stability, and low cost per dose. The vaccine can accomplish some or all of these features by combining the antigen with the adjuvant as discussed below.

a. Adjuvant

The vaccine can comprise an adjuvant. The molecular adjuvant can be a transcriptional factor, co-stimulatory molecule, chemokine or cytokines. The molecular adjuvant can be Rel-A, T-bet, Eomes, FLT3L, TWEAK, GITRL, STING or combinations thereof.

The adjuvant can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the adjuvant by a peptide bond. The amino acid sequence can be a protein, a peptide, a variant thereof, a fragment thereof, or a combination thereof.

(1) REL-A

The adjuvant can be transcription factor Rel-A (RelA). Rel-A and c-Rel possess transcriptional activating capabilities. In particular, Rel-A has been a vital component in inflammation and cell survival. In vitro experiments show that Rel-A potently activates KB-dependent transcription. This vital transcriptional factor regulates the gene expression of multiple inflammatory factors and survival factors that may orchestrate improved adaptive immunity. Rel-A, also known as p65, is encoded by the Rel-A gene in humans.

Rel-A is part of the NF-κB complex. NF-kB1 (p50) or NF-κB2 (p52) is bound to c-Rel, Rel-A (also known as p65), or Rel-B to form the NF-κB complex. This dimer resides within the cellular cytoplasm bound to its inhibitor I-κB. External stimuli induce the phosphorylation of the inhibitor and its ubiquitin mediated degradation by the 26S Proteasome. The released NF-κB then migrates into the nucleus to induce transcriptional gene activation.

NF-κB is a dimeric transcriptional factor that controls the transcription of DNA. NF-κB is found in almost all animal cell types and is involved in cellular responses to stimuli such as stress, cytokines, free radicals, ultraviolet irradiation, oxidized LDL, and bacterial or viral antigens. NF-κB plays a key role in regulating the immune response to infection (kappa light chains are critical components of immunoglobulins). Incorrect regulation of NF-κB has been linked to cancer, inflammatory and autoimmune diseases, septic shock, viral infection, and improper immune development. NF-κB has also been implicated in processes of synaptic plasticity and memory.

Rel-A can trigger the gene expression of type I IFNs, IFN-inducible chemokines, and proinflammatory cytokines, such as tumor necrosis factor-a (TNF-a) via distinct signaling pathways. Inclusion of Rel-A in the vaccine can induce IFN-γ production by at least about 0.5-fold, at least about 1.0-fold, 1.5-fold, at least about 2-fold, at least about 3-fold, at least about 4-fold, at least about 5-fold, at least about 8-fold, and at least about 10-fold as compared to a vaccine not including Rel-A. Inclusion of Rel-A in the vaccine can induce IFN-γ production by at least about 2-fold as compared to a vaccine not including Rel-A. Inclusion of Rel-A in the vaccine can induce IFN-γ production by at least about 3-fold as compared to a vaccine not including Rel-A.

Rel-A can stimulate the T cell response pathways via higher production of IL-2. Rel-A can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self cells is implemented as IL-2 is required to discriminate between self and non-self.

Rel-A can further stimulate the adaptive immune system by increasing B-cell production of IgG.

Rel-A can increase or boost the cellular and/or humoral immune response to the antigen in a subject. The antigen is discussed in more detail below. In some instances, Rel-A can increase the cellular and/or humoral immune response to the antigen by about 75% to about 200%. Alternatively, Rel-A can increase the cellular and/or humoral immune response to the antigen may be increased by about 90% to about 130%. In still other alternative embodiments, Rel-A can increase the cellular and/or humoral immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, Rel-A can increase or boost the immune response to a particular antigen from a vaccine that is administered to a subject in need thereof by at least 0.5-fold, 1.0-fold, 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

In other instance, Rel-A can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

Rel-A may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding Rel-A can be from any number of organisms, for example, mouse (*Mus musculus*), macaque (*Macacac mulatta*), and human (*Homo sapiens*). The nucleic acid encoding Rel-A can be optimized with regards to codon usage and corresponding RNA transcripts. The nucleic acid encoding Rel-A can be codon and RNA optimized for expression. In some embodiments, the nucleic acid encoding Rel-A can include a Kozak sequence (e.g., GCC ACC) to increase the efficiency of translation. The nucleic acid encoding Rel-A can include multiple stop codons (e.g., TGA TGA) to increase the efficiency of translation termination. The nucleic acid encoding Rel-A can also include a nucleotide sequence encoding an IgE leader sequence. The IgE leader sequence can be located 5' to the Rel-A in the nucleic acid. In some embodiments, the nucleic acid encoding Rel-A is free of or does not contain a nucleotide sequence encoding the IgE leader sequence.

Rel-A can be the optimized nucleic acid sequence SEQ ID NO:1, which encodes for SEQ ID NO:2. In some embodiments, Rel-A can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:1. In other embodiments, Rel-A can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. Rel-A can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

Some embodiments relate to fragments of SEQ ID NO:1. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:1 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:1. Some embodiments relate to fragments that have 96% or greater identity to the fragments of Rel-A nucleic acid sequences herein. Some embodiments relate to fragments that have 97% or greater identity to the fragments of Rel-A nucleic acid sequences herein. Some embodiments relate to fragments that have 98% or greater identity to the fragments of Rel-A nucleic acid sequences herein. Some embodiments relate to fragments that have 99% or greater identity to the fragments of Rel-A nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:2 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:2 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:2. Some embodiments relate to fragments having 96% or greater identity to the fragments of Rel-A protein sequences herein. Some embodiments relate to fragments having 97% or greater identity to the fragments of Rel-A protein sequences herein. Some embodiments relate to fragments having 98% or greater identity to the fragments of Rel-A protein sequences herein. Some embodiments relate to fragments having 99% or greater identity to the fragments of Rel-A protein sequences herein. In some embodiments, fragments include a leader sequence, for example, an immunoglobulin leader sequence such as the IgE leader sequence. In some embodiments, the fragments are free of a leader sequence.

(2) T-bet

The adjuvant can be a transcription factor T-bet. T-box transcription factor TBX21, also known as T-bet, T-PET, TBET, and TBLYM, is a protein that in humans is encoded by the TBX21 gene. This gene is a member of a phylogenetically conserved family of genes that share a common DNA-binding domain, the T-box. T-box genes encode transcription factors involved in the regulation of developmental processes. T-bet is the human ortholog of mouse Tbx21/Tbet gene. Studies in mouse show that Tbx21 protein is a Th1 cell-specific transcription factor that controls the expression of the hallmark Th1 cytokine, interferon-gamma (IFN-γ). Expression of the human ortholog also correlates with IFN-γ expression in Th1 and natural killer cells, suggesting a role for this gene in initiating Th1 lineage development from naive Th precursor cells. Ectopic expression of T-bet both transactivates the IFN-γ gene and induces endogenous IFN-γ production. T-bet initiates Th1 lineage development from naive Thp cells both by activating Th1 genetic programs and by repressing the opposing Th2 programs.

T-bet can trigger the gene expression of type I IFNs, IFN-inducible chemokines, and proinflammatory cytokines, such as tumor necrosis factor-a (TNF-a) via distinct signaling pathways. Inclusion of T-bet in the vaccine can induce IFN-γ production by at least about 0.5-fold, at least about 1.0-fold, at least about 1.5-fold, at least about 2-fold, at least about 3-fold, at least about 4-fold, at least about 5-fold, at least about 8-fold, and at least about 10-fold as compared to a vaccine not including T-bet. Inclusion of T-bet in the vaccine can induce IFN-γ production by at least about 2-fold as compared to a vaccine not including T-bet. Inclusion of T-bet in the vaccine can induce IFN-γ production by at least about 3-fold as compared to a vaccine not including T-bet.

T-bet can stimulate the T cell response pathways via higher production of IL-2. T-bet can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self cells is implemented as IL-2 is required to discriminate between self and non-self.

T-bet can further stimulate the adaptive immune system by increasing B-cell production of IgG.

T-bet can increase or boost the immune response to the antigen in a subject. The antigen is discussed in more detail below. In some instances, T-bet can increase the immune response to the antigen by about 75% to about 200%. Alternatively, T-bet can increase the immune response to the antigen may be increased by about 90% to about 130%. In still other alternative embodiments, T-bet can increase the immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, T-bet can increase or boost the immune response to a particular antigen from a vaccine that is administered to a subject in need thereof by 0.5 fold, 1.0 fold, 1.5-fold, at least 2-fold, at least 2.5-fold, at least 3-fold, at least 4-fold, at least 5-fold, at least 6-fold, at least 7-fold, at least 8-fold, at least 9-fold, or at least 10-fold.

In other instance, T-bet can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

T-bet may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding T-bet can be from any number of organisms, for example, mouse (*Mus musculus*), macaque (*Macacac mulatta*), and human (*Homo sapiens*). The nucleic acid encoding T-bet can be optimized with regards to codon usage and corresponding RNA transcripts. The nucleic acid encoding T-bet can be codon and RNA optimized for expression. In some embodiments, the nucleic acid encoding T-bet can include a Kozak sequence (e.g., GCC ACC) to increase the efficiency of translation. The nucleic acid encoding T-bet can include multiple stop codons (e.g., TGA TGA) to increase the efficiency of translation termination. The nucleic acid encoding T-bet can also include a nucleotide sequence encoding an IgE leader sequence. The IgE leader sequence can be located 5' to the T-bet in the nucleic acid. In some embodiments, the nucleic acid encoding T-bet is free of or does not contain a nucleotide sequence encoding the IgE leader sequence.

T-bet can be the optimized nucleic acid sequence SEQ ID NO:3, which encodes for SEQ ID NO:4. In some embodiments, T-bet can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:3. In other embodiments, T-bet can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. T-bet can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4.

Some embodiments relate to fragments of SEQ ID NO:3. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:3. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:3 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:3. Some embodiments relate to fragments that have 96% or greater identity to the fragments of T-bet nucleic acid sequences herein. Some embodiments relate to fragments that have 97% or greater identity to the fragments of T-bet nucleic acid sequences herein. Some embodiments relate to fragments that have 98% or greater identity to the fragments of T-bet nucleic acid sequences herein. Some embodiments relate to fragments that have 99% or greater identity to the fragments of T-bet nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:4 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:4. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:4 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:4. Some embodiments relate to fragments having 96% or greater identity to the fragments of T-bet protein sequences herein. Some embodiments relate to fragments having 97% or greater identity to the fragments of T-bet protein sequences herein. Some embodiments relate to fragments having 98% or greater identity to the fragments of T-bet protein sequences herein. Some embodiments relate to fragments having 99% or greater identity to the fragments of T-bet protein sequences herein. In some embodiments, fragments include a leader sequence, for example, an immunoglobulin leader sequence such as the IgE leader sequence. In some embodiments, the fragments are free of a leader sequence.

(3) Eomesodermin (Eomes)

The adjuvant can be a transcription factor Eomes. Eomes possesses transcriptional activator capabilities. In particular, Eomes plays a key role in the proliferation of intermediate progenitor cells and their progeny during development in various species.

Eomes can induce the cellular and/or humoral immune response. Specifically, in vivo experiments show that Eomes is expressed in activated CD8+ T-cells as part of the antiviral response, and subsequently regulates maturation and effector functions. Eomes is also involved in the differentiation of CD8+ T-cells during the immune response, wherein Eomes is regulating the expression of lytic effector cells. In particular, Eomes can increase IFN-γ production in CD8+ T cells and NK cells. Furthermore, numerous studies suggest that Eomes, in addition to IFN-γ regulation, is critical for invoking the characteristics of the cytolytic effector lineage.

Eomes can trigger the gene expression of type I IFNs, IFN-inducible chemokines, and proinflammatory cytokines, such as tumor necrosis factor-a (TNF-a) via distinct signaling pathways. Inclusion of Eomes in the vaccine can induce IFN-γ production by at least about 0.5-fold, at least about 1.0-fold, at least about 1.5-fold, at least about 2-fold, at least about 3-fold, at least about 4-fold, at least about 5-fold, at least about 8-fold, and at least about 10-fold as compared to a vaccine not including T-bet. Inclusion of Eomes in the vaccine can induce IFN-γ production by at least about 2-fold as compared to a vaccine not including Eomes. Inclusion of Eomes in the vaccine can induce IFN-γ production by at least about 3-fold as compared to a vaccine not including Eomes.

Eomes can stimulate the T cell response pathways via higher production of IL-2. Eomes can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self-cells is implemented as IL-2 is required to discriminate between self and non-self.

Eomes can further stimulate the adaptive immune system by increasing B-cell production of IgG.

Eomes can increase or boost the immune response to the antigen in a subject. The antigen is discussed in more detail below. In some instances, Eomes can increase the immune response to the antigen by about 75% to about 200%. Alternatively, Eomes can increase the immune response to the antigen may be increased by about 90% to about 130%. In still other alternative embodiments, Eomes can increase the immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, Eomes can increase or boost the immune response to a particular antigen from a vaccine that is administered to a subject in need thereof by 0.5 fold, 1.0 fold, 1.5-fold, at least 2-fold, at least 2.5-fold, at least 3-fold, at least 4-fold, at least 5-fold, at least 6-fold, at least 7-fold, at least 8-fold, at least 9-fold, or at least 10-fold.

In other instance, Eomes can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

Eomes may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding Eomes can be from any number of organisms, for example, mouse (*Mus musculus*), macaque (*Macacac mulatta*), and human (*Homo sapiens*). The nucleic acid encoding Eomes can be optimized with regards to codon usage and corresponding RNA transcripts. The nucleic acid encoding Eomes can be codon and RNA optimized for expression. In some embodiments, the nucleic acid encoding Eomes can include a Kozak sequence (e.g., GCC ACC) to increase the efficiency of translation. The nucleic acid encoding Eomes can include multiple stop codons (e.g., TGA TGA) to increase the efficiency of translation termination. The nucleic acid encoding Eomes can also include a nucleotide sequence encoding an IgE leader sequence. The IgE leader sequence can be located 5' to the Eomes in the nucleic acid. In some embodiments, the nucleic acid encoding Eomes is free of or does not contain a nucleotide sequence encoding the IgE leader sequence.

Eomes can be the optimized nucleic acid sequence SEQ ID NO:5, which encodes for SEQ ID NO:6. In some embodiments, Eomes can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:5. In other embodiments, Eomes can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. Eomes can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6.

Some embodiments relate to fragments of SEQ ID NO:5. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:5. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:5 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:5. Some embodiments relate to fragments that have 96% or greater identity to the fragments of Eomes nucleic acid sequences herein. Some embodiments relate to fragments that have 97% or greater identity to the fragments of Eomes nucleic acid sequences herein. Some embodiments relate to fragments that have 98% or greater identity to the fragments of Eomes nucleic acid sequences herein. Some embodiments relate to fragments that have 99% or greater identity to the fragments of Eomes nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:6 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:6. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:6 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:6. Some embodiments relate to fragments having 96% or greater identity to the fragments of Eomes protein sequences herein. Some embodiments relate to fragments having 97% or greater identity to the fragments of Eomes protein sequences herein. Some embodiments relate to fragments having 98% or greater identity to the fragments of Eomes protein sequences herein. Some embodiments relate to fragments having 99% or greater identity to the fragments of Eomes protein sequences herein. In some embodiments, fragments include a leader sequence, for example, an immunoglobulin leader sequence such as the IgE leader sequence. In some embodiments, the fragments are free of a leader sequence.

(4) FLT3L

The adjuvant can be FLT3L. FLT3L is a hematopoietic cytokine. FLT3L is a member of the class III receptor tyrosine kinase family. FLT3L is expressed in bone marrow stroma cells and myeloid cells, both of which are of B- and T-cell origin.

FLT3L plays a key role in the regulation of the cellular and/or humoral immune response. In particular, FLT3L demonstrates a role in the link between innate and adapative immunity with a role in regulating dendritic cells. In particular, FLT3L controls the development of dendritic cells, wherein FLT3L is important for plasmacytoid dendritic cells and CD8. Furthermore, FLT3L induces massive expansion of both myeloid and lymphoid dendritic cells in mice, as well as humans.

Dendritic cells are potent producers of IFN-γ. Accordingly, FLT3L can upregulate expression of IFN-γ, at the very least, by its regulation of dendritic cells.

FLT3L can induce the cellular and/or humoral immune response. Specifically, in vivo experiments show that FLT3L is expressed in activated CD8+ T-cells as part of the antiviral response, and subsequently regulates maturation and effector functions. FLT3L is also involved in the differentiation of CD8+ T-cells during the immune response, wherein FLT3L is regulating the expression of lytic effector cells. In particular, FLT3L can increase IFN-γ production in CD8+ T cells and NK cells. Furthermore, numerous studies suggest that FLT3L, in addition to IFN-γ regulation, is critical for invoking the characteristics of the cytolytic effector lineage.

FLT3L can trigger the gene expression of type I IFNs, IFN-inducible chemokines, and proinflammatory cytokines, such as tumor necrosis factor-a (TNF-a) via distinct signaling pathways. Inclusion of FLT3L in the vaccine can induce IFN-γ production by at least about 0.5-fold, at least about 1.0-fold, at least about 1.5-fold, at least about 2-fold, at least about 3-fold, at least about 4-fold, at least about 5-fold, at least about 8-fold, and at least about 10-fold as compared to a vaccine not including T-bet. Inclusion of FLT3L in the vaccine can induce IFN-γ production by at least about 2-fold as compared to a vaccine not including FLT3L. Inclusion of FLT3L in the vaccine can induce IFN-γ production by at least about 3-fold as compared to a vaccine not including FLT3L.

FLT3L can stimulate the T cell response pathways via higher production of IL-2. FLT3L can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self-cells is implemented as IL-2 is required to discriminate between self and non-self.

FLT3L can further stimulate the adaptive immune system by increasing B-cell production of IgG.

FLT3L can increase or boost the immune response to the antigen in a subject. The antigen is discussed in more detail below. In some instances, FLT3L can increase the immune response to the antigen by about 75% to about 200%. Alternatively, FLT3L can increase the immune response to the antigen may be increased by about 90% to about 130%. In still other alternative embodiments, FLT3L can increase the immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, FLT3L can increase or boost the immune response to a particular antigen from a vaccine that is administered in need thereof by 0.5 fold, 1.0 fold, 1.5-fold, at least 2-fold, at least 2.5-fold, at least 3-fold, at least 4-fold, at least 5-fold, at least 6-fold, at least 7-fold, at least 8-fold, at least 9-fold, or at least 10-fold.

In other instance, FLT3L can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

FLT3L may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding FLT3L can be from any number of organisms, for example, mouse (*Mus musculus*), macaque (*Macacac mulatta*), and human (*Homo sapiens*). The nucleic acid encoding FLT3L can be optimized with regards to codon usage and corresponding RNA transcripts. The nucleic acid encoding FLT3L can be codon and RNA optimized for expression. In some embodiments, the nucleic acid encoding FLT3L can include a Kozak sequence (e.g., GCC ACC) to increase the efficiency of translation. The nucleic acid encoding FLT3L can include multiple stop codons (e.g., TGA TGA) to increase the efficiency of translation termination. The nucleic acid encoding FLT3L can also include a nucleotide sequence encoding an IgE leader sequence. The IgE leader sequence can be located 5' to the FLT3L in the nucleic acid. In some embodiments, the nucleic acid encoding FLT3L is free of or does not contain a nucleotide sequence encoding the IgE leader sequence.

FLT3L can be the optimized nucleic acid sequence SEQ ID NO:7, which encodes for SEQ ID NO:8. In some embodiments, FLT3L can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:7. In other embodiments, FLT3L can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. FLT3L can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8.

Some embodiments relate to fragments of SEQ ID NO:7. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:7. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:7 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:7. Some embodiments relate to fragments that have 96% or greater identity to the fragments of FLT3L nucleic acid sequences herein. Some embodiments relate to fragments that have 97% or greater identity to the fragments of FLT3L nucleic acid sequences herein. Some embodiments relate to fragments that have 98% or greater identity to the fragments of FLT3L nucleic acid sequences herein. Some embodiments relate to fragments that have 99% or greater identity to the fragments of FLT3L nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:8 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:8. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:8 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:8. Some embodiments relate to fragments having 96% or greater identity to the fragments of FLT3L protein sequences herein. Some embodiments relate to fragments having 97% or greater identity to the fragments of FLT3L protein sequences herein. Some embodiments relate to fragments having 98% or greater identity to the fragments of FLT3L protein sequences herein. Some embodiments relate to fragments having 99% or greater identity to the fragments of FLT3L protein sequences herein. In some embodiments, fragments include a leader sequence, for example, an immunoglobulin leader sequence such as the IgE leader sequence. In some embodiments, the fragments are free of a leader sequence.

(5) TWEAK

The adjuvant can be TWEAK. TWEAK is a member of the tumor necrosis family. TWEAK is a multi-functional cytokine and its signaling involves its high affinity binding with the receptor fibroblast growth factor inducible 14 kDa protein, Fn14/TWEAKR. Specifically, TWEAK is involved with the cellular functions including, but not limited to, inhibition of cell differentiation, cell motility (e.g. migration, invasion), cell atrophy, cell proliferation, cell survival and inflammatory response.

TWEAK plays a key role in the regulation of the cellular and/or humoral immune response. In particular, leukocytes of the innate and adaptive immune response release TWEAK. Subsequently, TWEAK binds to Fn14/TWEAKR, which is upregulated in injured and/or diseased tissues. The complex of TWEAK and Fn14/TWEAKR then regulates the cellular responses as listed above. Additionally, TWEAK can be involved with dendritic cell survival, as well as dendritic cell and T-cell activation.

TWEAK can be modulated by IFN-γ. Studies show that IFN-γ stimulated monocytes result in a marked increase of TWEAK expression.

TWEAK can induce the cellular and/or humoral immune response. Specifically, in vivo experiments show that TWEAK is expressed in activated CD8+ T-cells as part of the anti-viral response, and subsequently regulates maturation and effector functions. TWEAK is also involved in the differentiation of CD8+ T-cells during the immune response, wherein TWEAK is regulating the expression of lytic effector cells. In particular, TWEAK can increase IFN-γ production in CD8+ T cells and NK cells. Furthermore, numerous studies suggest that TWEAK, in addition to IFN-γ regulation, is critical for invoking the characteristics of the cytolytic effector lineage.

TWEAK can trigger the gene expression of type I IFNs, IFN-inducible chemokines, and proinflammatory cytokines, such as tumor necrosis factor-a (TNF-a) via distinct signaling pathways. Inclusion of TWEAK in the vaccine can induce IFN-γ production by at least about 0.5-fold, at least about 1.0-fold, at least about 1.5-fold, at least about 2-fold, at least about 3-fold, at least about 4-fold, at least about 5-fold, at least about 8-fold, and at least about 10-fold as compared to a vaccine not including T-bet. Inclusion of TWEAK in the vaccine can induce IFN-γ production by at least about 2-fold as compared to a vaccine not including TWEAK. Inclusion of TWEAK in the vaccine can induce IFN-γ production by at least about 3-fold as compared to a vaccine not including TWEAK.

TWEAK can stimulate the T cell response pathways via higher production of IL-2. TWEAK can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self-cells is implemented as IL-2 is required to discriminate between self and non-self.

TWEAK can further stimulate the adaptive immune system by increasing B-cell production of IgG.

TWEAK can increase or boost the immune response to the antigen in a subject. The antigen is discussed in more detail below. In some instances, TWEAK can increase the immune response to the antigen by about 75% to about 200%. Alternatively, TWEAK can increase the immune response to the antigen may be increased by about 90% to about 130%. In still other alternative embodiments, TWEAK can increase the immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, TWEAK can increase or boost the immune response to a particular antigen from a vaccine that is administered to a subject in need thereof by 0.5 fold, 1.0 fold, 1.5-fold, at least 2-fold, at least 2.5-fold, at least 3-fold, at least 4-fold, at least 5-fold, at least 6-fold, at least 7-fold, at least 8-fold, at least 9-fold, or at least 10-fold.

In other instance, TWEAK can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

TWEAK may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding TWEAK can be from any number of organisms, for example, mouse (*Mus musculus*), macaque (*Macacac mulatta*), and human (*Homo sapiens*). The nucleic acid encoding TWEAK can be optimized with regards to codon usage and corresponding RNA transcripts. The nucleic acid encoding TWEAK can be codon and RNA optimized for expression. In some embodiments, the nucleic acid encoding TWEAK can include a Kozak sequence (e.g., GCC ACC) to increase the efficiency of translation. The nucleic acid encoding TWEAK can include multiple stop codons (e.g., TGA TGA) to increase the efficiency of translation termination. The nucleic acid encoding TWEAK can also include a nucleotide sequence encoding an IgE leader sequence. The IgE leader sequence can be located 5' to the TWEAK in the nucleic acid. In some embodiments, the nucleic acid encoding TWEAK is free of or does not contain a nucleotide sequence encoding the IgE leader sequence.

TWEAK can be the optimized nucleic acid sequence SEQ ID NO:9, which encodes for SEQ ID NO:10. In some embodiments, TWEAK can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:9. In other embodiments, TWEAK can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10. TWEAK can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10.

Some embodiments relate to fragments of SEQ ID NO:9. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:9. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:9 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:9. Some embodiments relate to fragments that have 96% or greater identity to the fragments of TWEAK nucleic acid sequences herein. Some embodiments relate to fragments that have 97% or greater identity to the fragments of TWEAK nucleic acid sequences herein. Some embodiments relate to fragments that have 98% or greater identity to the fragments of TWEAK nucleic acid sequences herein. Some embodiments relate to fragments that have 99% or greater identity to the fragments of TWEAK nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:10 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:10. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:10 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:10. Some embodiments relate to fragments having 96% or greater identity to the fragments of TWEAK protein sequences herein. Some embodiments relate to fragments having 97% or greater identity to the fragments of TWEAK protein sequences herein. Some embodiments relate to fragments having 98% or greater identity to the fragments of TWEAK protein sequences herein. Some embodiments relate to fragments having 99% or greater identity to the fragments of TWEAK protein sequences herein. In some embodiments, fragments include a leader sequence, for example, an immunoglobulin leader sequence such as the IgE leader sequence. In some embodiments, the fragments are free of a leader sequence.

(6) GITRL

The adjuvant can be GITRL. GITRL is a member of the tumor necrosis family that modulates natural and acquired immune response. GITRL is expressed on the cell surface of macrophages, dendritic cells, endothelial cells, and B cells. GITRL reacts with its cognate receptor GITR.

GITRL plays a key role in the regulation of the cellular and/or humoral immune response. Specifically, GITRL is expressed on T-cell and NK cells, wherein it is upregulated following cell activation. GITRL induced signaling is mediated by ERK1/2, which then triggers the activation of the transcription factor NF-κB. NF-κB controls the expression of several pro-inflammatory mediators, including chemokines, MMPs and cytokines.

GITRL can upregulate the expression of IFN-γ.

GITRL can induce the cellular and/or humoral immune response. Specifically, in vivo experiments show that GITRL is expressed in activated CD8+ T-cells as part of the anti-viral response, and subsequently regulates maturation and effector functions. GITRL is also involved in the differentiation of CD8+ T-cells during the immune response, wherein GITRL is regulating the expression of lytic effector cells. In particular, GITRL can increase IFN-γ production in CD8+ T cells and NK cells. Furthermore, numerous studies suggest that GITRL, in addition to IFN-γ regulation, is critical for invoking the characteristics of the cytolytic effector lineage.

GITRL can trigger the gene expression of type I IFNs, IFN-inducible chemokines, and proinflammatory cytokines, such as tumor necrosis factor-a (TNF-a) via distinct signaling pathways. Inclusion of GITRL in the vaccine can induce IFN-γ production by at least about 0.5-fold, at least about 1.0-fold, at least about 1.5-fold, at least about 2-fold, at least about 3-fold, at least about 4-fold, at least about 5-fold, at least about 8-fold, and at least about 10-fold as compared to a vaccine not including T-bet. Inclusion of GITRL in the vaccine can induce IFN-γ production by at least about 2-fold as compared to a vaccine not including GITRL. Inclusion of GITRL in the vaccine can induce IFN-γ production by at least about 3-fold as compared to a vaccine not including GITRL.

GITRL can stimulate the T cell response pathways via higher production of IL-2. GITRL can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self-cells is implemented as IL-2 is required to discriminate between self and non-self.

GITRL can further stimulate the adaptive immune system by increasing B-cell production of IgG.

GITRL can increase or boost the immune response to the antigen in a subject. The antigen is discussed in more detail below. In some instances, GITRL can increase the immune response to the antigen by about 75% to about 200%. Alternatively, GITRL K can increase the immune response to the antigen may be increased by about 90% to about 130%. In still other alternative embodiments, GITRL can increase the immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, GITRL can increase or boost the immune response to a particular antigen from a vaccine that is administered to a subject in need thereof by 0.5 fold, 1.0 fold, 1.5-fold, at least 2-fold, at least 2.5-fold, at least 3-fold, at least 4-fold, at least 5-fold, at least 6-fold, at least 7-fold, at least 8-fold, at least 9-fold, or at least 10-fold.

In other instance, GITRL can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

GITRL may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding GITRL can be from any number of organisms, for example, mouse (*Mus musculus*), macaque (*Macacac mulatta*), and human (*Homo sapiens*). The nucleic acid encoding GITRL can be optimized with regards to codon usage and corresponding RNA transcripts. The nucleic acid encoding GITRL can be codon and RNA optimized for expression. In some embodiments, the nucleic acid encoding GITRL can include a Kozak sequence (e.g., GCC ACC) to increase the efficiency of translation. The nucleic acid encoding GITRL can include multiple stop codons (e.g., TGA TGA) to increase the efficiency of translation termination. The nucleic acid encoding GITRL can also include a nucleotide sequence encoding an IgE leader sequence. The IgE leader sequence can be located 5' to the GITRL in the nucleic acid. In some embodiments, the nucleic acid encoding GITRL is free of or does not contain a nucleotide sequence encoding the IgE leader sequence.

GITRL can be the optimized nucleic acid sequence SEQ ID NO:11, which encodes for SEQ ID NO:12. In some embodiments, GITRL can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:11. In other embodiments, GITRL can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12. GITRL can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12.

Some embodiments relate to fragments of SEQ ID NO:11. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:11. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:11 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:11. Some embodiments relate to fragments that have 96% or greater identity to the fragments of GITRL nucleic acid sequences herein. Some embodiments relate to fragments that have 97% or greater identity to the fragments of GITRL nucleic acid sequences herein. Some embodiments relate to fragments that have 98% or greater identity to the fragments of GITRL nucleic acid sequences herein. Some embodiments relate to fragments that have 99% or greater identity to the fragments of GITRL nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:12 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:12. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:12 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:12. Some embodiments relate to fragments having 96% or greater identity to the fragments of GITRL protein sequences herein. Some embodiments relate to fragments having 97% or greater identity to the fragments of GITRL protein sequences herein. Some embodiments relate to fragments having 98% or greater identity to the fragments of GITRL protein sequences herein. Some embodiments relate to fragments having 99% or greater identity to the fragments of GITRL protein sequences herein. In some embodiments, fragments include a leader sequence, for example, an immunoglobulin leader sequence such as the IgE leader sequence. In some embodiments, the fragments are free of a leader sequence.

(7) STING

The adjuvant can be STING. STING is a transmembrane protein that has a key role in the cellular and/or humoral immune response. STING is a DNA sensor that is activated when a cell confronts a dsDNA, resulting in the upregulation of type 1 IFN in the absence of TLRs. Type 1 IFN is essential for optimal DNA vaccine-induced immunity because it stimulates antigen-specific B-cells and CD4+ and CD8+ T-cells. It has been shown that STING is necessary for the effective production of type 1 IFN.

STING can upregulate expression of IFN-γ.

STING can induce the cellular and/or humoral immune response. Specifically, in vivo experiments show that STING is expressed in activated CD8+ T-cells as part of the anti-viral response, and subsequently regulates maturation and effector functions. STING is also involved in the differentiation of CD8+ T-cells during the immune response, wherein STING is regulating the expression of lytic effector cells. In particular, STING can increase IFN-γ production in CD8+ T cells and NK cells. Furthermore, numerous studies suggest that STING, in addition to IFN-γ regulation, is critical for invoking the characteristics of the cytolytic effector lineage.

STING can trigger the gene expression of type I IFNs, IFN-inducible chemokines, and proinflammatory cytokines, such as tumor necrosis factor-a (TNF-a) via distinct signaling pathways. Inclusion of STING in the vaccine can induce IFN-γ production by at least about 0.5-fold, at least about 1.0-fold, at least about 1.5-fold, at least about 2-fold, at least about 3-fold, at least about 4-fold, at least about 5-fold, at least about 8-fold, and at least about 10-fold as compared to a vaccine not including T-bet. Inclusion of STING in the vaccine can induce IFN-γ production by at least about 2-fold as compared to a vaccine not including STING. Inclusion of STING in the vaccine can induce IFN-γ production by at least about 3-fold as compared to a vaccine not including STING.

STING can stimulate the T cell response pathways via higher production of IL-2. STING can stimulate the growth, proliferation, and differentiation of T cells to become 'effector' T cells and the expression of IL-2 receptors IL-2R. The IL-2/IL-2R interaction then stimulates the growth, differentiation and survival of antigen-specific CD4+ T cells and CD8+ T cells. By stimulating IL-2, the immune system regulation between self and non-self-cells is implemented as IL-2 is required to discriminate between self and non-self.

STING can further stimulate the adaptive immune system by increasing B-cell production of IgG.

STING can increase or boost the immune response to the antigen in a subject. The antigen is discussed in more detail below. In some instances, STING can increase the immune response to the antigen by about 75% to about 200%. Alternatively, STING can increase the immune response to the antigen may be increased by about 90% to about 130%. In still other alternative embodiments, STING can increase the immune response to the antigen may be increased by 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without adjuvant.

In other embodiments, STING can increase or boost the immune response to a particular antigen from a vaccine that is administered to a subject in need thereof by 0.5 fold, 1.0 fold, 1.5-fold, at least 2-fold, at least 2.5-fold, at least 3-fold, at least 4-fold, at least 5-fold, at least 6-fold, at least 7-fold, at least 8-fold, at least 9-fold, or at least 10-fold.

In other instance, STING can modify or alter immune system recognition of at least one epitope in the antigen in any number of tissues in the individual, for example, a skin tissue and a muscle tissue. The antigen is described in more detail below. Such altered recognition of the at least one epitope can induce a greater immune response in a subject administered the herein described vaccines as compared to a subject administered a vaccine comprising a nucleic acid corresponding to the antigen alone.

STING may also modify or change the presentation of one or more epitopes in the antigen, for example, by allowing a previously unrecognized epitope to be recognized by the immune system, thereby increasing the immune response in the subject to the antigen. The modified presentation, and thus the increased immune response, can occur in any number of tissues in the subject, for example, a skin tissue and a muscle tissue.

A nucleic acid encoding STING can be from any number of organisms, for example, mouse (*Mus musculus*), macaque (*Macacac mulatta*), and human (*Homo sapiens*). The nucleic acid encoding STING can be optimized with regards to codon usage and corresponding RNA transcripts. The nucleic acid encoding STING can be codon and RNA optimized for expression. In some embodiments, the nucleic acid encoding STING can include a Kozak sequence (e.g., GCC ACC) to increase the efficiency of translation. The nucleic acid encoding STING can include multiple stop codons (e.g., TGA TGA) to increase the efficiency of translation termination. The nucleic acid encoding STING can also include a nucleotide sequence encoding an IgE leader sequence. The IgE leader sequence can be located 5' to the STING in the nucleic acid. In some embodiments, the nucleic acid encoding STING is free of or does not contain a nucleotide sequence encoding the IgE leader sequence.

STING can be the optimized nucleic acid sequence SEQ ID NO:13, which encodes for SEQ ID NO:14. In some embodiments, STING can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:13. In other embodiments, STING can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:14. STING can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:14.

Some embodiments relate to fragments of SEQ ID NO:13. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:13. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:13 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:13. Some embodiments relate to fragments that have 96% or greater identity to the fragments of STING nucleic acid sequences herein. Some embodiments relate to fragments that have 97% or greater identity to the fragments of STING nucleic acid sequences herein. Some embodiments relate to fragments that have 98% or greater identity to the fragments of STING nucleic acid sequences herein. Some embodiments relate to fragments that have 99% or greater identity to the fragments of STING nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:14 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:14. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:14 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:14. Some embodiments relate to fragments having 96% or greater identity to the fragments of STING protein sequences herein. Some embodiments relate to fragments having 97% or greater identity to the fragments of STING protein sequences herein. Some embodiments relate to fragments having 98% or greater identity to the fragments of STING protein sequences herein. Some embodiments relate to fragments having 99% or greater identity to the fragments of STING protein sequences herein. In some embodiments, fragments include a leader sequence, for example, an immunoglobulin leader sequence such as the IgE leader sequence. In some embodiments, the fragments are free of a leader sequence.

b. Antigen

The vaccine can comprise an antigen or fragment or variant thereof. The antigen can be anything that induces an immune response in a subject. Purified antigens are not usually strong immunogenic on their own and are therefore combined with the adjuvant as described above. The immune response induced by the antigen can be boosted or increased when combined with the adjuvant. Such an immune response can be a humoral immune response and/or a cellular immune response. In some embodiments, the combination of the adjuvant and the antigen can boost or increase a cellular immune response in the subject.

The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). Preferably, the antigen can be associated with influenza or HIV.

Some antigens can induce a strong immune response. Other antigens can induce a weak immune response. The antigen can elicit a greater immune response when combined with the adjuvant as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, or cancer causing virus.

(a) Hepatitis Antigen

The adjuvant can be associated or combined with a hepatitis virus antigen (i.e., hepatitis antigen), or fragment thereof, or variant thereof. The hepatitis antigen can be an antigen or immunogen from hepatitis A virus (HAV), hepatitis B virus (HBV), hepatitis C virus (HCV), hepatitis D virus (HDV), and/or hepatitis E virus (HEV). In some embodiments, the hepatitis antigen can be a heterologous nucleic acid molecule(s), such as a plasmid(s), which encodes one or more of the antigens from HAV, HBV, HCV, HDV, and HEV. The hepatitis antigen can be full-length or immunogenic fragments of full-length proteins.

The hepatitis antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus hepatitis antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The hepatitis antigen can be a consensus HBV core protein, or a consensus HBV surface protein.

In some embodiments, the hepatitis antigen can be a HBV genotype A consensus core DNA sequence construct, an IgE leader sequence linked to a consensus sequence for HBV genotype A core protein, or a HBV genotype A consensus core protein sequence.

In other embodiments, the hepatitis antigen can be a HBV genotype B consensus core DNA sequence construct, an IgE leader sequence linked to a consensus sequence for HBV genotype B core protein, or a HBV genotype B consensus core protein sequence.

In still other embodiments, the hepatitis antigen can be a HBV genotype C consensus core DNA sequence construct, an IgE leader sequence linked to a consensus sequence for HBV genotype C core protein, or a HBV genotype C consensus core protein sequence.

In some embodiments, the hepatitis antigen can be a HBV genotype D consensus core DNA sequence construct, an IgE leader sequence linked to a consensus sequence for HBV genotype D core protein, or a HBV genotype D consensus core protein sequence.

In other embodiments, the hepatitis antigen can be a HBV genotype E consensus core DNA sequence construct, an IgE leader sequence linked to a consensus sequence for HBV genotype E core protein, or a HBV genotype E consensus core protein sequence.

In some embodiments, the hepatitis antigen can be a HBV genotype F consensus core DNA sequence construct, an IgE leader sequence linked to a consensus sequence for HBV genotype F core protein, or a HBV genotype F consensus core protein sequence.

In other embodiments, the hepatitis antigen can be a HBV genotype G consensus core DNA sequence construct, an IgE leader sequence linked to a consensus sequence for HBV genotype G core protein, or a HBV genotype G consensus core protein sequence.

In some embodiments, the hepatitis antigen can be a HBV genotype H consensus core DNA sequence construct, an IgE leader sequence linked to a consensus sequence for HBV genotype H core protein, or a HBV genotype H consensus core protein sequence.

In still other embodiments, the hepatitis antigen can be a HBV genotype A consensus surface DNA sequence construct, an IgE leader sequence linked to a consensus sequence for HBV genotype A surface protein, or a HBV genotype A consensus surface protein sequence.

In some embodiments, the hepatitis antigen can be a HBV genotype B consensus surface DNA sequence construct, an IgE leader sequence linked to a consensus sequence for HBV genotype B surface protein, or a HBV genotype B consensus surface protein sequence.

In other embodiments, the hepatitis antigen can be a HBV genotype C consensus surface DNA sequence construct, an IgE leader sequence linked to a consensus sequence for HBV genotype C surface protein, or a HBV genotype C consensus surface protein sequence.

In still other embodiments, the hepatitis antigen can be a HBV genotype D consensus surface DNA sequence construct, an IgE leader sequence linked to a consensus sequence for HBV genotype D surface protein, or a HBV genotype D consensus surface protein sequence.

In some embodiments, the hepatitis antigen can be a HBV genotype E consensus surface DNA sequence construct, an IgE leader sequence linked to a consensus sequence for HBV genotype E surface protein, or a HBV genotype E consensus surface protein sequence.

In other embodiments, the hepatitis antigen can be a HBV genotype F consensus surface DNA sequence construct, an IgE leader sequence linked to a consensus sequence for HBV genotype F surface protein, or a HBV genotype F consensus surface protein sequence.

In still other embodiments, the hepatitis antigen can be a HBV genotype G consensus surface DNA sequence construct, an IgE leader sequence linked to a consensus sequence for HBV genotype G surface protein, or a HBV genotype G consensus surface protein sequence.

In other embodiments, the hepatitis antigen can be a HBV genotype H consensus surface DNA sequence construct, an IgE leader sequence linked to a consensus sequence for HBV genotype H surface protein, or a HBV genotype H consensus surface protein sequence.

(b) Human Papilloma Virus (HPV) Antigen

The adjuvant can be associated or combined with a human papilloma virus (HPV) antigen, or fragment thereof, or variant thereof. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof (c) RSV Antigen The adjuvant can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be an optimized amino acid RSV F amino acid sequence, or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be an optimized amino acid RSV G amino acid sequence, or fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein 2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, for the RSV M2-2 protein from the RSV Long strain, the RSV L protein from the RSV Long strain, the RSV G protein from the RSV subtype B isolate H5601, the RSV G protein from the RSV subtype B isolate H1068, for the RSV G protein from the RSV subtype B isolate H5598, the RSV G protein from the RSV subtype B isolate H1123, or fragment thereof, or variant thereof.

(d) Influenza Antigen

The adjuvant can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen a protein comprising a consensus H1 amino acid sequence or a consensus H2 amino acid sequence. The consensus hemagglutinin antigen may be a synthetic hybrid consensus H1 sequences comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements.

The consensus hemagglutinin antigen may further comprise on its N-terminal an IgE or IgG leader amino acid sequence. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. In some embodiments, consensus hemagglutinin antigen may further comprise on its N-terminal an IgE or IgG leader amino acid sequence and on its C terminal an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or a an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can be facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

(e) Human Immunodeficiency Virus (HIV) Antigen

The adjuvant can be associated or combined with an HIV antigen or fragment thereof, or variant thereof. HIV antigens can include modified consensus sequences for immunogens. Genetic modifications including codon optimization, RNA optimization, and the addition of a high efficient immunoglobin leader sequence to increase the immunogenicity of constructs can be included in the modified consensus sequences. The novel immunogens can be designed to elicit stronger and broader cellular immune responses than a corresponding codon optimized immunogens.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(2) Parasite Antigens

The adjuvant can be associated or combined with a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: Acanthamoeba keratitis, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be Acanthamoeba, Anisakis, *Ascaris lumbricoides*, Botfly, *Balantidium coli*, Bedbug, Cestoda (tapeworm), Chiggers, *Cochliomyia hominivorax*, *Entamoeba histolytica*, *Fasciola hepatica, Giardia lamblia*, Hookworm, *Leishmania, Linguatula serrata*, Liver fluke, Loa loa, *Paragonimus*—lung fluke, Pinworm, *Plasmodium falciparum*, Schistosoma, *Strongyloides stercoralis*, Mite, Tapeworm, *Toxoplasma gondii, Trypanosoma*, Whipworm, or *Wuchereria bancrofti*.

(a) Malaria Antigen

The adjuvant can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS; LSA1; TRAP; CelTOS; and Ama1. The immunogens may be full length or immunogenic fragments of full length proteins. The immunogens comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA Tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA Tag.

In further embodiments, the malaria antigen can be Ama1, which is a highly conserved *Plasmodium* antigen. The malaria antigen can also be a consensus sequence of Ama1 (i.e., ConAma1 immunogen) comprising in some instances, a signal peptide such as an immunoglobulin signal peptide such as an IgE or IgG signal peptide and in some embodiments, may comprise an HA Tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA Tag.

In other embodiments, the malaria antigen can be a fusion proteins comprising a combination of two or more of the PF proteins set forth herein. For example, fusion proteins may comprise two or more of Consensus CS immunogen, ConLSA1 immunogen, ConTRAP immunogen, ConCelTOS immunogen and, ConAma1 immunogen linked directly adjacent to each other or linked with a spacer or one more amino acids in between. In some embodiments, the fusion protein comprises two PF immunogens; in some embodiments the fusion protein comprises three PF immunogens, in some embodiments the fusion protein comprises four PF immunogens, and in some embodiments the fusion protein comprises five PF immunogens. Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1.

Fusion proteins with five Consensus PF immunogens may comprise CS or CS-alt, LSA1, TRAP, CelTOS and Ama1.

In some embodiments, the fusion proteins comprise a signal peptide linked to the N terminus. In some embodiments, the fusion proteins comprise multiple signal peptides linked to the N terminal of each Consensus PF immunogens. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein wherein the spacer is a proteolyic cleavage site recognized by a protease found in cells to which the vaccine is intended to be administered and/or taken up and the fusion proteins comprises multiple signal peptides linked to the N terminal of each Consensus PF immunogens such that upon cleavage the signal peptide of each Consensus PF immunogens translocates the Consensus PF immunogen to outside the cell.

(3) Bacterial Antigens

The adjuvant can be associated or combined with a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-*Thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, psychrophile, halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis*, methicillin-resistant *Staphylococcus aureus* (MRSA), or *Clostridium difficile*.

(a) *Mycobacterium tuberculosis* Antigens

The adjuvant can be associated or combined with a *Mycobacterium tuberculosis* antigen (i.e., TB antigen or TB immunogen), or fragment thereof, or variant thereof. The TB antigen can be from the Ag85 family of TB antigens, for example Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW. In some embodiments, the TB antigen can be heterologous nucleic acid molecules such as plasmids, which encode one or more of the *Mycobacterium tuberculosis* immunogens from the Ag85 family and the Esx family. The immunogens can be full-length or immunogenic fragments of full-length proteins. The immunogens can comprise consensus sequences and/or modifications for improved expression. Consensus immunogens may comprise a signal peptide such as an immunoglobulin signal peptide such as an IgE or IgG signal peptide and in some embodiments, may comprise an HA tag.

(4) Fungal Antigens

The adjuvant can be associated or combined with a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii*, dermatophyte, *Fusarium* species, *Histoplasma capsulatum*, Mucoromycotina, *Pneumocystis jirovecii, Sporothrix schenckii, Exserohilum*, or *Cladosporium.* c. Vector

The vaccine can comprise one or more vectors that include one or more heterologous nucleic acids encoding the antigen and the adjuvant. The one or more vectors can be capable of expressing the antigen and the adjuvant. The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular heterologous nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing heterologous DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, or one or more desired adjuvants. The LEC may be any linear DNA devoid of any phosphate backbone. The DNA may encode one or more antigens, or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

The LEC may be derived from any plasmid capable of being linearized. The plasmid may be capable of expressing the antigen, or the adjuvant. The plasmid may be capable of expressing the adjuvant Rel-A and/or T-bet. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise a pharmaceutically acceptable excipient. The pharmaceutically acceptable excipient can be functional molecules such as vehicles, adjuvants other than Rel-A, T-bet, Eomes, FLT3L, TWEAK, GITRL and STING, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate is may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to Rel-A, T-bet, Eomes, FLT3L, TWEAK, GITRL and STING. The additional adjuvant can be other genes that are expressed in an alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants in addition to Rel-A, T-bet, Eomes, FLT3L, TWEAK, GITRL and STING include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. Methods of Vaccination

The present invention is also directed to methods of increasing an immune response in a subject by different routes of administration by the vaccine. Increasing the immune response can be used to treat and/or prevent disease in the subject.

The method can include administering the herein disclosed vaccines to the subject. The subject administered the vaccine can have an increased or boosted immune response as compared to a subject administered the antigen alone. In some embodiments, the immune response in the subject administered the vaccine can be increased by about 18% to about 650%. Alternatively, the immune response in the subject administered the vaccine may be increased by about 45% to about 260%. In still other alternative embodiments, the immune response in the subject administered the vaccine may be increased by about 93% to about 130%.

In other embodiments, the administered vaccine can increase or boost the immune response in the subject by at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

The vaccine can induce IFN-γ production by at least about 1.5-fold, at least about 2-fold, at least about 3-fold, at least about 4-fold, at least about 5-fold, at least about 8-fold, and at least about 10-fold as compared to a vaccine not including the adjuvant.

The vaccine can increase or boost the cellular and/or humoral immune response to the antigen in a subject as compared to a vaccine without the adjuvant. The vaccine can increase the cellular and/or humoral immune response to the antigen by about 75% to about 200%. Alternatively, the vaccine can increase the cellular and/or humoral immune response to the antigen may be increased by about 90% to about 130% as compared to a vaccine without the adjuvant. The vaccine can increase the cellular and/or humoral immune response to the antigen may be increased by about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200% as compared to a vaccine without the adjuvant.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccines can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. No. 6,520,950; U.S. Pat. No. 7,171,264; U.S. Pat. No. 6,208,893; U.S.

Pat. No. 6,009,347; U.S. Pat. No. 6,120,493; U.S. Pat. No. 7,245,963; U.S. Pat. No. 7,328,064; and U.S. Pat. No. 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

4. Examples

Example 1

Materials and Methods for Examples 2-4

Plasmid Vaccine Constructs.

The pRelA plasmid DNA constructs encode the full-length mouse NF-κB subunit p65/RelA (GenBank #TF65_MOUSE) and Type-1 transactivator T-bet (GenBank #TBX21_MOUSE), respectively. In addition, the Ig heavy chain epsilon-1 signal peptide (GenBank#AAB59424) was fused to the N-terminus of each sequence, replacing the N-terminal methionine, which facilitates expression. Each gene was genetically optimized for expression in mice, including codon- and RNA-optimization, among other proprietary modifications for enhancing protein expression (GenScript, Piscataway, N.J., USA). The optimized genes were then sub-cloned into modified pVax1 mammalian expression vectors (Invitrogen, Carlsbad, Calif., USA) under the control of the cytomegalovirus immediate-early (CMV) promoter. These reagents were then used as the molecular adjuvants in this study. The pGag and pEnv plasmids, expressing the HIV-1 proteins Gag and Env respectively.

Transfections and Western Blot Analysis.

Human Embryonic Kidney (HEK) 293T cells were maintained in Dulbecco's modified Eagle medium (Life Technologies, Grand Island, N.Y., USA), supplemented with 10% heat-inactivated fetal calf serum (FCS), 100 IU of penicillin per mL, 100 μg of streptomycin per mL and 2 mM L-glutamine. Briefly, cells were transfected using TurboFection 8.0 (OriGene, Rockville, Md., USA) per the manufacturer's protocol and subsequently incubated for 24-48 h. Cells were harvested with ice cold PBS, centrifuged and washed, and then pelleted for Western immunoblot analysis. Nuclear extracts ($10^7$ cells) were made. The nuclear proteins from the transfected cells were then dissolved in 20 mM Hepes (pH 7.9) containing 0.4 M NaCl, 1 mM EDTA, 1 mM EGTA, 1 mM DTT, 1 mM PMSF and a cocktail of protease inhibitors (Promega Corp, Madison, Wis., USA). The protein concentration of each extract was measured by the Bio-Rad protein assay kit (Bio-Rad, Hercules, Calif., USA), and extracts were stored in aliquots at −70° C. until used. Standard western blotting analysis was performed. Cells were treated with protein lysis buffer (0.01 M Tris-HCl buffer pH 7.4, containing 1% Triton X-100, 1% sodium deoxycholate, 0.1% SDS) supplemented with protease inhibitors (Protease Inhibitor Cocktail tablets; Roche, Indianapolis, Ind., USA). Proteins in lysates were then separated using 12% SDS-PAGE. Protein-specific detection antibodies for RelA and T-bet (Cell Signaling Technology, Danvers, Mass., USA) were incubated with the blots and expression visualized using the enhanced chemiluminescence (ECL) Western blot detection system (GE Healthcare, Piscataway, N.J., USA).

Confirmation of Transcription Activity of RelA/p65 and T-bet by Luciferase Reporter Assay and IFN-Gamma Production.

A RelA/p65 expressing vector, which co-expresses luciferase (pNF-κB-Luc) was used to confirm the functionality of RelA/p65, which is necessary before it being used the "adjuvanted" vaccine study. The luciferase reporter assay was performed. Briefly, 293T cells ($10^5$ cells/well)

were seeded in a 96-well plate for 24 h. The cells were then transfected with the RelA/p65 Luc expressing plasmid followed by incubation for 6 hrs. After incubation, the cell culture medium was removed and replaced with fresh medium. Two days post transfection cells were treated with 20 ng/mL of recombinant TNF-α for 6 h followed by measurement of luciferase activity by using Microlumat plus luminometer (LUMAT LB9501, Berthold Technologies, Oak Ridge, Tenn., USA). For confirmation of pT-bet function, the production of IFN-γ from pT-bet transfected CD4+ T cells was measured. The impetus for measurement of IFN-γ is based on previously published studies that demonstrated a direct correlation between T-bet and IFN-γ production. Briefly in this analysis naïve CD4+ T cells, isolated from the spleens of Balb/C mice, were purified using a CD4+ T cell isolation kit (Miltenyibiotec, San Diego, Calif., USA). These cells were maintained in RPMI media supplemented with 10% FBS, 100 U/mL penicillin and 200 µg/mL streptomycin and subsequently transfected with pT-bet or pVax1 as a negative control. Two days post-transfection, cells were stimulated overnight with anti-CD3 plus anti-CD28 Abs (1 µg/mL). IFN-γ levels in the supernatants collected from the cultured CD4+ T cells were subsequently measured by a standard ELISA.

Analysis and Vaccination Regimen.

Adult female BALB/cJ (H-2d) mice were purchased from The Jackson Laboratory (Bar Harbor, Me., USA). Mice were immunized intramuscularly (i.m.) by needle injection into the left-thigh quadriceps muscle with 25 µg of plasmid resuspended in 25 µL of PBS. Vaccinations were immediately followed by EP, at the same site, and repeated at a two-week interval. For EP mediate delivery, a three-pronged CELLECTRA® adaptive constant current Minimally Invasive Device (MID) was used, supplied by Inovio Pharmaceuticals, Inc. (Blue Bell, Pa., USA). Specifically, square-wave pulses were delivered through a triangular 3-electrode array (inserted 2 mm intradermally) consisting of 26-gauge solid stainless steel electrodes and two constant-current pulses of 0.1 Amps were delivered for 52 msec/pulse separated by a 1 s delay. During the vaccination/molecular adjuvant administration regimen, and through the termination for the study, all mice were monitored every 3 days for the development of potential adverse effects.

Splenocyte, T Cell Isolation, and Cytokine Quantitation.

Spleens were harvested 7-8 days following the third immunization. Briefly, spleens were placed in RPMI 1640 medium (Mediatech, Manassas, Va., USA) supplemented with 10% FBS, 1× Antibiotic-Antimycotic (Life Technologies, Grand Island, N.Y., USA), and 1×β-ME (Life Technologies, Grand Island, N.Y., USA). Splenocytes were isolated by mechanical disruption of the spleen using a Stomacher machine (Seward Laboratory Systems, Bohemia, N.Y., USA), and the resulting product was filtered using a 40 µm cell strainer (BD Biosciences, San Jose, Calif., USA). The cells were then treated for 5 min with ACK lysis buffer (Lonza, Walkersville, Md., USA) for lysis of RBCs, washed in PBS, and then resuspended in RPMI medium for use in the ELISPOT assay. CD4 naïve T cells were purified from the spleens using a naïve CD4+ T cell isolation kit (Miltenyi Biotec, Auburn, Calif., USA). These cells were maintained in RPMI medium supplemented with 10% FBS, 100 U/mL penicillin, 200 µg/mL streptomycin, and stimulated with anti-CD3 plus anti-CD28 (1 µg/mL each). Upon stimulation with anti-CD3 plus anti-CD28 antibodies, cytokine production levels in the culture supernatants of cultured cells were examined by enzyme-linked immunosorbent assay (ELISA).

ELISPOT Analysis.

A standard IFN-γ ELISPOT assay was used in this study. Briefly, 96-well plates (Millipore, Billerica, Mass., USA) were coated with anti-mouse IFN-γ capture antibody and incubated for 24 h at 4° C. (R&D Systems, Minneapolis, Minn., USA). The following day, plates were washed with PBS and then incubated for 2 h with blocking buffer (1% BSA and 5% sucrose in PBS). CD4+ or CD8+ T cells (5×105 cells/well plated in triplicate) were MACS-purified (Miltenyibiotec, San Diego, Calif., USA) from splenocytes and subsequently stimulated with HIV-1 Gag (consensus subtype B) or Env (subtype B (MN)) peptides (15-mers overlapping by 11 amino acids, spanning the lengths of their respective protein (NIH AIDS Reagent Program, Bethesda, Md., USA). After 18-24 h of stimulation overnight at 37° C. in 5% CO2, the plates were washed in PBS and subsequently incubated for an additional 24 h at 4° C. with biotinylated anti-mouse IFN-γ monoclonal antibody (mAb) purchased from R&D Systems (Minneapolis, Minn., USA). The plates were then washed again in PBS, and streptavidin-alkaline phosphatase (MabTech, Nacka Strand, Sweden) was added to each well and incubated for 2 h at RT. Lastly, the plates were washed again in PBS followed by incubation with BCIP/NBT Plus substrate (MabTech, Cincinnati, Ohio, USA) for 5-30 min. Upon completion of spot development based on visual inspection, the plate was rinsed with distilled water and then dried overnight at RT. Spots were enumerated using an automated ELISPOT reader (Cellular Technology, Shaker Heights, Ohio, USA).

T Cell Proliferation Assay.

Proliferative responses were measured in vitro by incubating 105 splenocytes in culture medium per well in 96-well U-bottom plates in the presence of serial dilutions (5, 1, and 0.1 µg/mL) of recombinant HIV-1 IIIB pr55 (Gag) (NIH AIDS Reagent Program, Bethesda, Md.) or HIV-1 MN IIIB gp160 (Env) (Protein Sciences, Meriden, Conn., USA) and incubated at 37° C. with 5% CO2. Incorporation of tritiated (3H)-thymidine was measured by pulsing with µCi/well of (3H)-thymidine during a 0-24 h time period. The plate was then harvested and incorporated 3H-thymidine was measured in a Beta plate reader (Wallac, Waltham, Mass., USA). The proliferative response is expressed as a stimulation index (SI), calculated by dividing the mean cpm (counts per minute) of Ag-stimulated wells by the mean cpm of non-stimulated wells.

ELISA.

Sera from vaccinated mice harvested 7 days following the third vaccination were tested for antibody responses against recombinant HIV-1 Env (NIH AIDS Reagent Program) by ELISA. Briefly, 96-well ELISA plates were coated with recombinant HIV-1 Env protein (Protein Sciences) and incubated at 4° C. and washed subsequently with PBS and 0.1% Tween-20. Plates were then blocked for 2 h with PBS and 0.2% Tween-20. After removal of the blocking solution, 100 µL of the pre-diluted (1:50, 1:100, 1:500, 1:1000) mouse serum was added and incubated for 1 h. Plates were then washed four times and incubated with a peroxidase-coupled anti-mouse IgG mAb (Sigma-Aldrich, St. Louis, Mo., USA). Lastly, plates were washed again followed by addition of 200 µl of substrate solution (R&D Systems, Minneapolis, Minn., USA) per well. The optical density at (OD405 nm) was subsequently measured after a 15 min incubation. All assays were performed in triplicate.

Flow Cytometry.

Muscle tissues (i.e., from the site of injection/vaccination) were removed aseptically, rinsed in Hanks' balanced salt solution (Life Technologies, Grand Island, N.Y., USA), minced into approximately 1×2-mm squares, and digested in 20 mL of collagenase A (1 mg/mL, Life Technologies, Grand Island, N.Y., USA) at 37° C. for 45 min, with occasional agitation. The cellular digest was filtered through a sterile 31 µm nylon mesh, centrifuged at 400 g for 10 min, and washed twice in 10% FCS-DMEM. The cell pellet was then resuspended in 4 mL of 10% FCS-DMEM.

For flow cytometric analysis, $10^6$ cells from the immunized mice cells were washed in suspension with ice-cold buffer A (PBS/0.1% BSA/0.01% NaN3) and incubated for 20 min at 4° C. with 50 µL of a 1:100 diluted fluorescent-labeled specific antibodies. The fluorescently conjugated Abs utilized were FITC-CD11c, PE-CD4, PE-Cy7-CD45R (B220) (eBioscience, San Diego, Calif., USA), Alexa Fluor-750-CD8a, and PerCP-Cy5.5-CD11b (BD Biosciences, San Jose, Calif., USA). Cells were washed twice and immediately analyzed on a flow cytometer (Becton Dickinson FACS, San Jose, Calif., USA). All incubations and washes were performed at 4° C. with icecold buffer A. Cells were gated on singlets and live cells. The flow cytometric data were analyzed using FlowJo software (Tree Star, Ashland, Oreg., USA).

Statistical Analysis.

Group analyses were completed by a matched, two-tailed, unpaired t-test with all values are presented as mean±SEM. Mann-Whitney analysis was used to determine statistical differences. All data were analyzed using Prism software (GraphPad Prism5). (GraphPad Prism, La Jolla, Calif., USA). Statistically significant differences between groups were defined as $*p<0.1$, $p<0.01$, $*p<0.001$, and $****p<0.0001$.

Example 2

Adjuvant Construction and Expression

Figure 1:
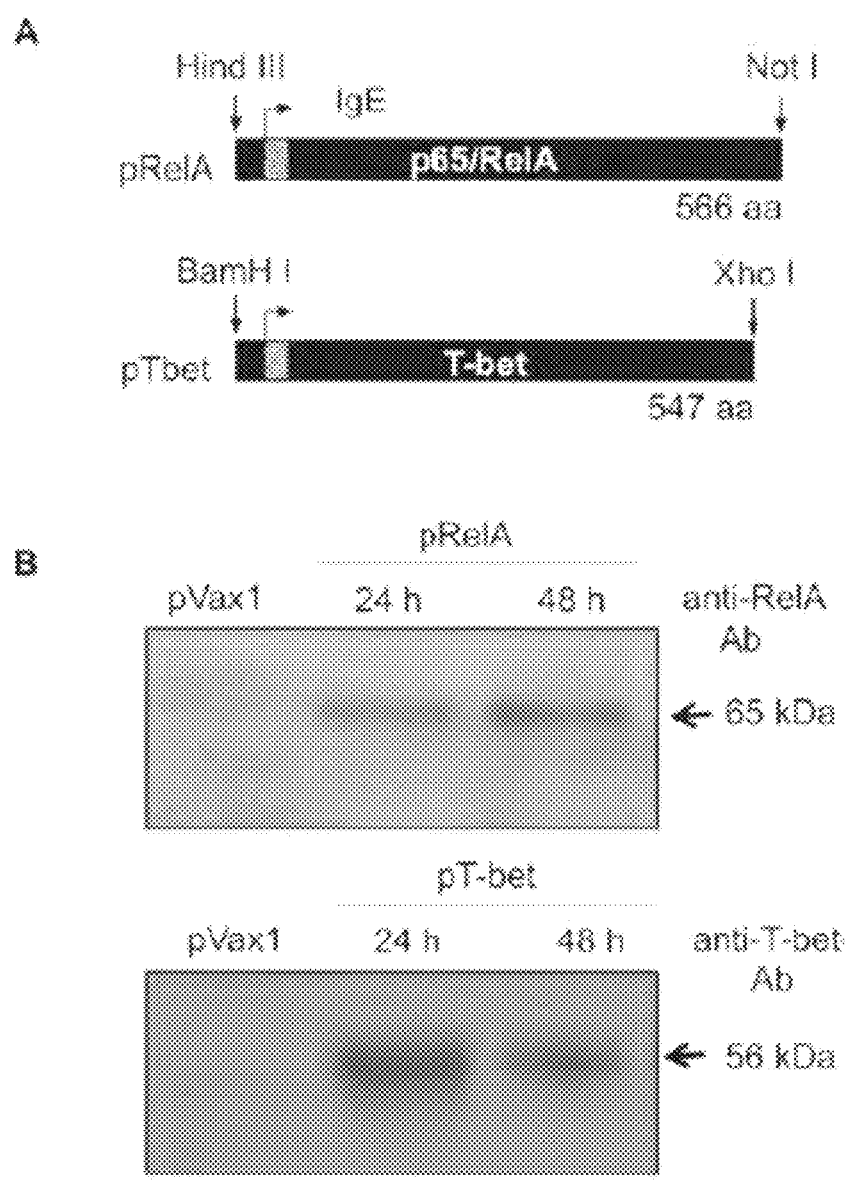
FIG. 1 shows molecular adjuvant construction and expression and confirmation. (A) Mouse RelA or T-bet primary sequences were genetically optimized, synthesized, and then subcloned into modified pVax1 expression vectors. Optimization entailed inclusion of a IgE leader peptide (IgE), preceded by a Kozak sequence, fused at the N-terminus. The figure indicates the restrictions enzymes used for subcloning, the translation initiation site (forward arrow), IgE leader peptide (IgE; hatched bar), protein length (aa), and transgenes (black with white lettering); (B) Protein expression from the nuclear extract was analyzed by Western immunoblotting following transfection of HEK 293T cells with pRelA, pTbet, or empty vector control (pVax1). The relative size (kDa) of the proteins were determined by detection analysis using protein-specific Abs as indicated; (C) Over expression of RelA potently induced KB dependent transcription. HeLa cells were transiently transfected with a NF-κB-dependent luciferase reporter gene together with expression vectors encoding RelA/p65. The cotransfected cells were subsequently grown for 48 h, and the luciferase activity was determined as described in Example 1; (D). Overexpression of T-bet stimulated production of IFN-γ: Naive CD4 T cells were transfected with either pT-bet or pVax1 and stimulated with anti-CD3 plus anti-CD28 followed the measurement of IFN-γ production by enzyme-linked immunosorbent assay (ELISA) as described in Example 1. IFN-γ levels are expressed as µg/mL

The pRelA and pTbet plasmids encode the full-length mouse NF-kappa B subunit p65/RelA and Type-1 transactivator T-bet, respectively. Each was genetically optimized, synthesized, and subcloned into modified pVax1 mammalian expression vectors (FIG. 1A). To test for expression of these plasmids, HEK 293T cells were transfected with each and protein production was assessed by standard Western immunoblotting. An approximately 65 kDa protein corresponding to RelA was detected, using a specific Ab, in cell lysates harvested both 24 h and 48 h post-transfection (FIG. 1B). Likewise, T-bet was detected as an approximately 56 kDa protein using an anti-T-bet Ab. Binding was specific for their respective proteins since neither bound to lysates from cells transfected with empty vector control plasmid pVax1. These data demonstrated that each of the molecular adjuvants expresses their respective encoded proteins upon in vitro transfection of HEK 293T cells. Further, IκB-dependent transcription was assessed in the HeLa cells luciferase expressing cell system (FIG. 1C) to confirm the activation of RelA (p65). An increase in RelA expression as measured by relative luciferase activity was observed in a dose dependent manner That is, increasing the plasmid from 3 µg to 5 µg or 10 µg resulted in an increase in the relative luciferase activity approximately 1.5 or 2.5 fold. T-bet expression correlated with IFN-γ expression in T cell and NK cells and therefore in this assay IFN-γ served as surrogate for the functional expression of T-bet (FIG. 1D).

Additionally, immunofluorescence analysis (IFA) of the sub-cellular localization of RelA protein expression following transfection of HeLa cells with pRelA plasmid and stained with anti-NF-κB (p65) antibody is shown in FIG. 6. This IFA further confirmed expression of RelA from the pRelA plasmid.

Example 3

Enhanced Cellular Immunity

Figure 2:
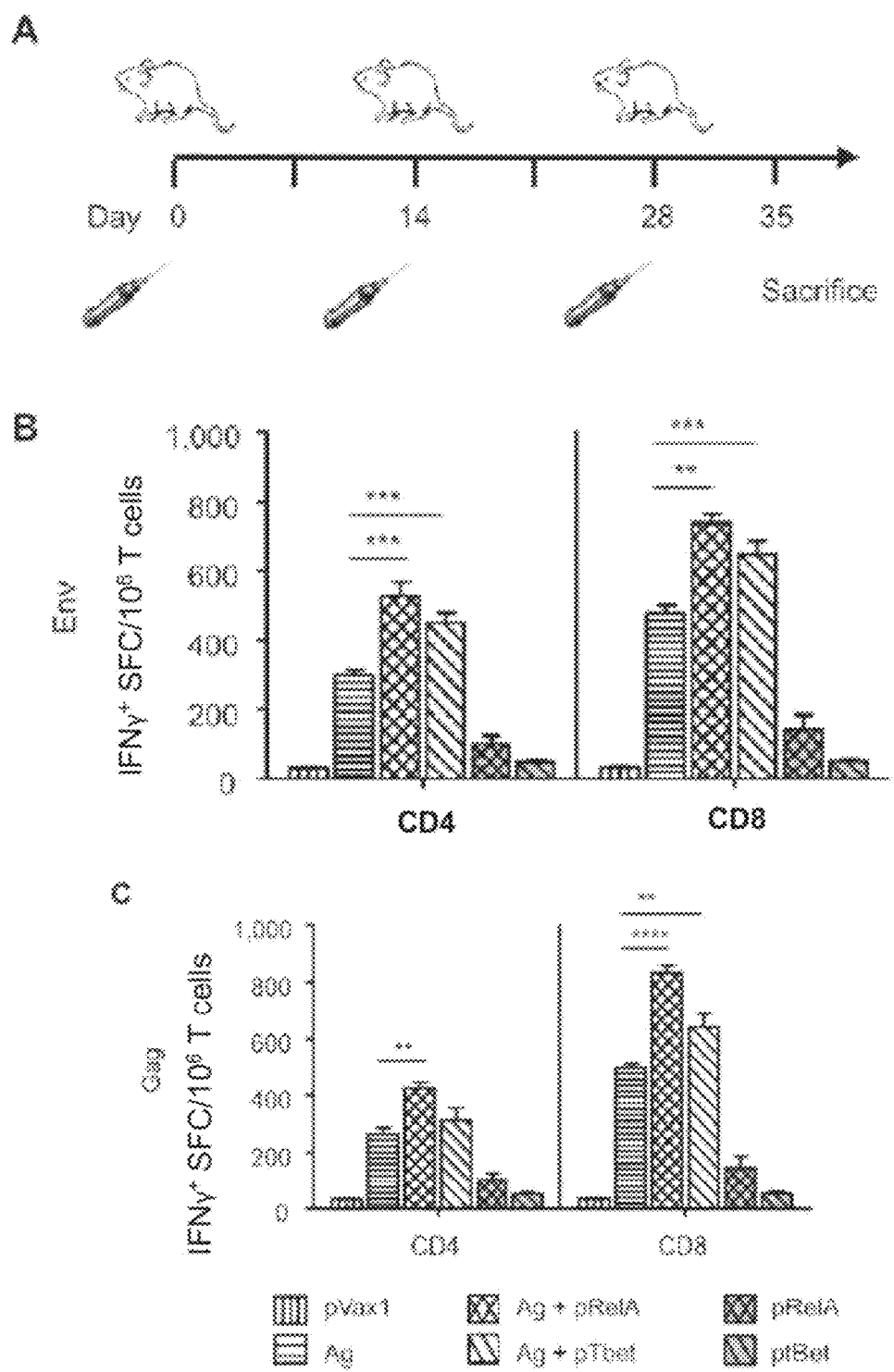
FIG. 2 shows transcription factor adjuvanted antigen specific DNA vaccines enhances T cell immunity. (A) Balb/C mice (n=4/group) were vaccinated three times at two week intervals with HIV-1 pGag or pEnv alone, pGag or pEnv with co delivery of either pRelA or pTbet. Other control groups were pRelA or pTbet alone, or a pVax1 control. T-cell responses (CD8+ and CD4+) were analyzed by IFN-γ ELISPOT one week following the third immunization and results for IFN-γ+ spot forming cells (SFC) per 106 MACS-purified T-cells are indicated following re-stimulation with subtype B HIV-1 Env (B) or Gag (C) peptide pools. Samples were performed in triplicate, error bars represent SEM, and statistically significant values are shown; p<0.01, *p<0.001 and ****p<0.0001, referring to comparison between the indicated vaccination groups provided in the graph. Experiments were performed twice independently with similar results.

The contribution of pRelA and pTbet in terms of enhancing vaccine-induced immunity, was then assessed. Balb/C mice (n=4/group) were vaccinated three times with 25 µg of pEnv or pGag either with or without 25 µg of pRelA or pTbet, 25 µg of pRelA or pTbet alone, or with 25 µg of a control plasmid (pVax1; FIG. 2). The vaccines and adjuvants were delivered in 25 µL of PBS by in vivo EP. Animals were sacrificed on day 35, (i.e., 7 days after the third vaccination) followed by isolation of splenocytes for immune analysis by IFN-γ ELISpot. In this assay, HIV-1 Env or Gag peptide pools were used for stimulation of MACS-purified CD4+ or CD8+ T cells and the IFN-γ ELISpot results are displayed in FIG. 2. Both CD4+ and CD8+ T-cell responses were observed to be significantly increased in mice vaccinated with pEnv and co-administrated pRelA compared with pEnv alone. Likewise, immunization with pEnv with co-administrated pTbet compared to pEnv alone demonstrated significant increases in CD4+ and CD8+ T cell responses (FIG. 2B).

To confirm the enhancing effects of these two adjuvants on T cell IFN-γ production for a different Ag, we also vaccinated animals with the HIV-1Gag either with or without pRelA or pTbet, similarly as performed above. Analogous to the pEnv group, CD4+ T cell responses were increased in mice immunized with pGag plus co-administrated pRelA, when compared with mice immunized with pGag alone (FIG. 2C). There was an even greater enhancement of the CD8+ T cell response in mice vaccinated with pGag and co-administrated pRelA compared to immunization with pGag alone (FIG. 2C). Further, immunization with HIV-1 Gag along with concomitant administration of pTbet demonstrated increased CD8+ T-cell responses when compared to immunization with pGag alone (FIG. 2C). However, CD4+ T cell responses were not as significantly increased as observed with co-delivery of pRelA. Also, administration of either pRelA or pTbet alone did not markedly activate either CD4+ or CD8+ T cells against Gag or Env as measured by IFN-γ production. Therefore, these data demonstrated that co-administration of the transcription factor adjuvants promoted enhanced T cell responses against two separate antigens with the data suggesting that expanding the breadth of vaccine-elicited cellular immune responses was stimulated by administration of an immune adjuvant.

Since the RelA molecular adjuvant was observed to particularly enhance T cell responses, the proliferative potential of cells immunized in the presence or absence of pRelA was evaluated. Splenocytes from vaccinated animals were harvested at 7 days following the third immunization and were then stimulated with their cognate Ag, i.e., either HIV-1 Env or Gag (FIG. 3). In pEnv-vaccinated mice, there was a trend towards enhanced proliferation at all Ag doses in mice that also received the pRelA adjuvant when compared to unadjuvanted animals (FIG. 3A). This trend was also observed in pGag-vaccinated animals where the overall stimulation index was higher when pRelA was co-delivered (FIG. 3B). As well, in both FIG. 3A,B, in addition to the overall stimulation index, fold increase graphs are included, with the 'fold" value being a ratio of stimulation index of the pEnv+pRelA or pGag+pRelA groups divided by stimulation indexes of the pEnv or pGag alone groups. Thus, the stimulation index in pEnv and pGag vaccinated animals was increased by the inclusion of a pRelA adjuvant, at all vaccine doses tested. These responses were specific for the HIV Ags since minimal proliferation was observed in splenocytes from animals that received the pRelA adjuvant alone. Taken together, these results demonstrated that the pRelA DNA adjuvant enhances Ag-specific T cell proliferative responses against two individual specific antigens.

Additionally, FIG. 7 shows the concentration of interleukin-2 (IL-2) in pg/mL from mice immunized with vaccine that did or not include the adjuvant RelA. These data demonstrated that inclusion of RelA in the vaccine significantly increased IL-2 production by about 3-fold.

Example 4

Enhanced Antibody Responses with Adjuvanted Vaccination

Based on the observed adjuvant mediated increase in T cell IFN-γ and proliferative responses, the effects of these molecular adjuvants on B-cell induction was evaluated. HIV-1 Env-specific IgG was measured in the sera of vaccinated animals 7 days following the third vaccination. As indicated, mice received pEnv either with or without co-administered pRelA or pTbet, pRelA or pTbet alone, or a pVax1 control plasmid (FIG. 4). Measurable IgG responses were induced by pEnv alone at dilutions ranging from 1:50 to 1:500, but were non longer measurable at a dilution of 1:1,000. These responses were augmented at all dilutions by the inclusion of the pRelA or pTbet adjuvant when compared to the pEnv group alone. Specifically, differences were observed at the 1:50 sera dilution, where administration of pRelA and pTbet significantly enhanced the induction of HIV-1 Env-specific IgG responses (p=0.0388 and p=0.0062, respectively). Enhanced IgG responses were specific for Env since minimal antibody responses were observed in the sera from mice that were administered the pRelA or pTbet adjuvant alone. These data suggest that both transcription factor adjuvants elicited an enhanced humoral immune response that was analogous and consistent with the elevated IFN-γ levels and T cell proliferative responses observed following vaccination with pRelA or pTbet.

FIG. 8A shows increased humoral immune responses of Balb/C mice coimmunized with pRelA. ELISA analysis of sera from mice immunized with plasmid DNA encoding pVax1, pEnv or pEnv+pRelA. IgG antibody reactivity against gp120 in sera from DNA-inoculated mice was measured by an ELISA. Mice were either immunized 3 immunization once. OD405, optical density at 405 nm. FIG. 8B shows differential effect of RelA on isotype switching to IgG subclasses. Splenic Env and Env+RelA cells expressing totalIgG1 and IgG2 was determined. The values represent the means±SEM of five independent experiments. The values represent the means±SEM of three independent experiments.

FIG. 8C shows increased humoral immune responses of Balb/C mice coimmunized with pRelA. ELISA analysis of sera from mice immunized with plasmid DNA encoding pVax1, pEnv or pEnv+pT-bet. IgG antibody reactivity against gp120 in sera from DNA-inoculated mice was measured by an ELISA. Mice were either immunized 3 immunization once. OD405, optical density at 405 nm. FIG. 8D shows differential effect of T-bet on isotype switching to IgG subclasses. Splenic Env and Env+ T-bet cells expressing totalIgG1 and IgG2 was determined. The values represent the means±SEM of five independent experiments. The values represent the means±SEM of three independent experiments.

One potential mechanism for the ability of the transcription factors to enhance antibody responses can be thorough an increase in the number of activated B-cells. To assess whether this was occurring, the pRelA administered muscle at the site of vaccination was biopsied 3 days after pEnv immunization with co-administered pRelA followed by quantification of number of B220+ B-cells at the site of injection. FIG. 9 shows the relative expression (in percentage). The results indicated that pRelA and pEnv alone caused only a slight increase in B-cell trafficking to the site of injection compared to pVax1 administration alone (FIG. 5). This was indicated by the MFI (mean fluorescent intensity) values shown in the individual FACS scans, which are directly proportional to the level of B220+ B cells. However, the addition of a pRelA adjuvant in combination with the pEnv vaccine further enhanced the number of B-cells at the site of injection.

In summary, the data in Examples 2-4 demonstrated the use of cellular transcription factors RelA and T-bet as molecular adjuvants for enhancing DNA vaccine-induced immunity. When co-delivered along with a prototypical DNA vaccine by in vivo electroporation (EP), either of these adjuvants stimulated enhanced antigen-specific T and B cell responses as indicated by increased T cell numbers and IFN-γ production, as well as by an increase in antibody levels. Co-administration of either pRelA or pTbet in conjunction with the pEnv or pGag vaccine significantly increased T cell immunity, as measured by INF-γ production by ELISpot and proliferation. As well, B-cell/antibody levels were enhanced as indicated by an increase in B-cell numbers as well as antigen specific antibody titers. Consistent with these findings, the total amount of antigen specific IgG in serum was increased following the co-administration of plasmids expressing the transcription factors.

Example 5

Cellular Response with TWEAK or GITRL as an Adjuvant

A pTWEAK plasmid was constructed by optimizing the codon usage of the nucleotide sequence encoding full-length TWEAK. This optimized nucleotide sequence was then cloned into the pVAX1 expression vector at the BamHI and EcoRI restriction sites.

A pGITRL plasmid was constructed by optimizing the codon usage of the nucleotide sequence encoding full-length GITRL. This optimized nucleotide sequence was then cloned into the pVAX1 expression at the BamHI and EcoRI restriction sites.

Ten groups of mice were included in the study. Four mice were in each group and the mice in each group were 6-8 week old female Balb/c mice. One group was immunized with antigen alone (i.e., 15 µg of DNA encoding HIV-1 Env), one group was immunized with 15 µg of DNA encoding HIV-1 Env and 7.5 µg of pTWEAK ("T"), one group was immunized with 15 µg of DNA encoding HIV-1 Env and 10 µg of pTWEAK ("T"), one group was immunized with 15 µg of DNA encoding HIV-1 Env and 7.5 µg of pGITRL ("G"), and one group was immunized with 15 µg of DNA encoding HIV-1 Env and 10 µg of pGITRL ("G").

Immunizations were done intramuscularly (IM) followed by electroporation with the MID-EP system. Specifically, for each immunization, 25 μg of DNA was injected using an insulin syringe with a 29-gauge needle. One week after each immunization, mice were bled by retro-orbital bleeding.

The immunization regimen is shown schematically in FIG. 10. Mice were given a priming immunization at day 0 and then booster immunizations at day 14 and day 28. Mice were sacrificed at day 35 to harvest a final bleed for ELISA analysis and splenocytes for ELSspot analysis.

The results of the ELISspot analysis are shown in FIGS. 11 and 12 for TWEAK and GITRL, respectively. These data demonstrated that TWEAK increased the cellular immune response (as evidenced by increased IFN-γ levels) to the antigen as compared to the vaccine lacking TWEAK. These data also demonstrated that GITRL increased the cellular immune response (as evidenced by increased IFN-γ levels) to the antigen as compared to the vaccine lacking GITRL. Accordingly, TWEAK and GITRL served as adjuvants that increased IFN-γ levels and the cellular immune response to the antigen as compared to the same vaccine lacking TWEAK or GITRL as an adjuvant.

Example 6

Humoral Immune Response with TWEAK or GITRL as an Adjuvant

The humoral immune response was examined in mice when TWEAK or GITRL was used as an adjuvant in the vaccine. The immunization scheduled described above in Example 5 and shown in FIG. 10 was used in this investigation. Humoral response was measured via ELISA, wherein the optical density was measured at OD450. All experimental groups showed a marked increase in optical density at a reciprocal titer dilution of up to approximately 158, relative to naïve. In particular, the 10 μg dose GITRL showed the most significant increase in humoral response with over a 3-fold increase of optical density at a reciprocal titer dilution of 50. Difference of experimental groups over control was mitigated when dilutions were increased above 5000.

Example 7

Cellular Response with EOMES as an Adjuvant

A pEOMES plasmid was constructed by optimizing the codon usage of the nucleotide sequence encoding EOMES. This optimized nucleotide sequence was then cloned into the pVAX1 expression vector at the BamHI and EcoRI restriction sites. An IgE leader sequence and Kozak sequence were also located 5' of the nucleotide sequence encoding EOMES. A schematic of the construct is shown in FIG. 14A.

Expression of EOMES from the pEOMES plasmid was confirmed by transfecting cells with the pEOMES plasmid and pVAX1 plasmid (negative control). As shown in FIG. 14B, EOMES was expressed in the cells transfected with pEOMES, but not the cells transfected with pVAX1. Expression was analyzed by western blotting of lysates two days post-transfection, in which cells had been transfected with 10 μg of DNA.

Groups of mice were included in the study. Five mice were in each group and the mice in each group were 6-8 week old female Balb/c mice. One group of mice was immunized with pVAX1 (negative control), one group was immunized with the antigen alone (i.e., DNA encoding HIV Env, plasmid referred to as pHIV-Env), and one group was immunized with pHIV-Env and pEOMES.

Immunizations were done intramuscularly (IM) followed by electroporation with the MID-EP system. Specifically, for each immunization, 25 μg of DNA was injected using an insulin syringe with a 29-gauge needle. One week after each immunization, mice were bled by retro-orbital bleeding.

The immunization regimen is shown schematically in FIG. 15. Mice were given a priming immunization at week 0 and then booster immunizations at week 2 and week 4. Mice were sacrificed at week 5 to harvest splenocytes for ELSspot analysis.

The results of the ELISspot analysis are shown in FIG. 16. These data demonstrated that EOMES increased the cellular immune response (as evidenced by increased IFN-γ levels) to the antigen as compared to the vaccine lacking EOMES. Accordingly, EOMES served as adjuvants that increased IFN-γ levels and the cellular immune response to the antigen as compared to the same vaccine lacking EOMES as an adjuvant.

Example 8

Cellular Response with STING as an Adjuvant

A pSTING plasmid was constructed by optimizing the codon usage of the nucleotide sequence encoding STING. This optimized nucleotide sequence was then cloned into the pVAX1 expression vector.

Expression of STING from the pSTING plasmid was confirmed by transfecting 293T cells with the pSTING plasmid and pVAX1 plasmid (negative control). As shown in FIG. 17, STING was expressed in the cells transfected with pSTING, but not the cells transfected with pVAX1. Expression was analyzed by western blotting of lysates two days post-transfection, in which cells had been transfected with 10 μg of DNA.

Groups of mice were included in the study. Four mice were in each group and the mice in each group were 6-8 week old female Balb/c mice. One group of mice was immunized with pVAX1 (negative control), one group was immunized with the antigen alone (i.e., DNA encoding HIV Env, plasmid referred to as pHIV-Env), one group was immunized with pHIV-Env and pSTING (20 μg), and one group was immunized with pHIV-Env and pSTING (50 μg).

Immunizations were done intramuscularly (IM) followed by electroporation with the MID-EP system. Specifically, for each immunization, DNA was injected using an insulin syringe with a 29-gauge needle. One week after each immunization, mice were bled by retro-orbital bleeding.

The immunization regimen is shown schematically in FIG. 18. Mice were given a priming immunization at week 0 and then booster immunizations at week 2 and week 4. Mice were sacrificed at week 5 to harvest splenocytes for ELSspot analysis.

The results of the ELISspot analysis are shown in FIG. 19. These data demonstrated that STING increased the cellular immune response (as evidenced by increased IFN-γ levels) to the antigen as compared to the vaccine lacking STING. Accordingly, STING served as adjuvants that increased IFN-γ levels and the cellular immune response to the antigen as compared to the same vaccine lacking STING as an adjuvant.

It is understood that the foregoing detailed description and accompanying examples are merely illustrative and are not

What is claimed is:

1. A vaccine comprising a nucleotide sequence encoding an antigen and a nucleotide sequence encoding Rel-A, wherein the nucleotide sequence encoding Rel-A comprises SEQ ID NO: 1.

2. The vaccine of claim 1, wherein the vaccine comprises a first nucleic acid molecule encoding the antigen and a second nucleic acid molecule encoding RelA.

3. The vaccine of claim 2, wherein the second nucleic acid molecule comprises an expression vector.

4. The vaccine of claim 1, wherein the antigen is selected from a group consisting of a human papilloma virus (HPV) antigen, an HIV antigen, an influenza antigen, a *Plasmodium falciparum* antigen and a fragment thereof.

5. The vaccine of claim 4, wherein the HIV antigen is selected from the group consisting of Env A, Env B, Env C, Env D, B Nef-Rev, Gag and any combination thereof.

6. The vaccine of claim 4, wherein the influenza antigen is selected from the group consisting of H1 HA, H2 HA, H3 HA, H5 HA, BHA antigen and any combination thereof.

7. The vaccine of claim 4, wherein the *Plasmodium falciparum* antigen includes a circumsporozoite (CS) antigen.

8. The vaccine of claim 4, wherein the HPV antigen is selected from the group consisting of HPV16 E6 antigen, an HPV16 E7 antigen, and a combination thereof.

9. The vaccine of claim 1, further comprising a pharmaceutically acceptable excipient.

10. A method for increasing an immune response in a subject, the method comprising administering the vaccine of claim 1 to the subject in need thereof.

11. The method of claim 10, wherein administering the vaccine includes at least one of intramuscular administration and intradermal administration.

12. The method of claim 10, wherein administering the vaccine includes electroporation.

13. The method of claim 10, wherein the immune response in the subject is increased by about 50% to about 150%.

14. The method of claim 13, wherein the immune response in the subject is increased by about 90% to about 130%.

15. The method of claim 14, wherein the immune response in the subject is increased by about 105%.

16. The method of claim 3, wherein the immune response in the subject is increased by at least about 2.5-fold.

17. The method of claim 3, wherein the immune response in the subject is increased by at least about 1.5 fold.

18. A nucleic acid molecule comprising nucleotide sequence SEQ ID NO: 1.

19. The nucleic acid molecule of claim 18, wherein the nucleic acid molecule is one or more plasmids.

* * * * *

SEQUENCE LISTING

<160> NUMBER OF SEQ ID NOS: 14

<210> SEQ ID NO 1
<211> LENGTH: 1704
<212> TYPE: DNA
<213> ORGANISM: Artificial Sequence
<220> FEATURE:
<223> OTHER INFORMATION: Synthetic construct, Rel-A

<400> SEQUENCE: 1

| | | | | | |
|---|---|---|---|---|---|
| atggattgga | cttggatctt | attttagtt | gctgctgcta | ctagagttca | ttctgacgat | 60 |
| ctgtttcccc | tcatctttcc | ctcagagcca | gcccaggctt | ctgggcctta | tgtggagatc | 120 |
| atcgaacagc | cgaagcaacg | gggcatgcga | ttccgctata | aatgcgaggg | gcgctcagcg | 180 |
| ggcagtattc | ctggcgagag | aagcacagat | accaccaaga | cacaccccac | catcaagatc | 240 |
| aatggctaca | caggaccagg | aacagttcga | atctccctgg | tcaccaagga | tccacctcac | 300 |
| cggcctcatc | cacatgaact | tgtggggaag | gactgccggg | atggctacta | tgaggctgac | 360 |
| ctctgcccag | accgcagtat | ccatagcttc | cagaacctgg | ggatccagtg | tgtgaagaag | 420 |
| cgagacctgg | agcaagccat | tagccagcga | atccagacca | acaataaccc | ctttcacgtt | 480 |
| cctatagagg | agcagcgcgg | ggactatgac | ttgaatgcag | tgcgcctctg | cttccaggtg | 540 |
| acagtgcggg | acccagcagg | caggcccctc | ctcctgaccc | ctgtcctctc | acatccgatt | 600 |
| tttgataacc | gggcccccaa | cactgccgag | ctcaagatct | gccgagtaaa | ccggaactct | 660 |
| gggagctgcc | tcggtgggga | tgagatcttc | ttgctgtgcg | acaaggtgca | gaaagaagac | 720 |
| attgaggtgt | atttcacggg | accaggctgg | gaggcacgag | gctccttttc | tcaagctgat | 780 |
| gtgcatcggc | aagtggccat | tgtgttccgg | actcctccgt | acgccgaccc | cagcctccag | 840 |
| gctcctgttc | gagtctccat | gcagctacgg | cggccttctg | atcgcgagct | cagtgagccc | 900 |
| atggagttcc | agtacttgcc | agacacagat | gatcgccacc | ggattgaaga | gaagcgcaaa | 960 |
| aggacctatg | agaccttcaa | gagtatcatg | aagaagagtc | ctttcaatgg | accaactgaa | 1020 |
| ccccggcctc | caacccggcg | tattgctgtg | cctacccgaa | actcaacttc | tgtccccaag | 1080 |
| ccagcccgc | agcctacac | cttccagca | tccctcagca | ccatcaactt | tgatgagttt | 1140 |
| tcccccatgc | tgttaccatc | agggcagatc | tcaaaccagg | ccctggcctt | agcaccgtcc | 1200 |
| tctgccccag | tccttgccca | gaccatggtc | ccttcctcag | ccatggtacc | tctggctcag | 1260 |
| cccccagctc | ctgccccagt | tctaacccg | ggtcctcccc | agtccctgtc | tgcacctgtt | 1320 |
| ccaaagagca | cccaggctgg | ggaaggcacg | ctgtcggaag | ccctgctgca | cctgcagttt | 1380 |
| gatgctgatg | aagacttggg | ggccttgctt | ggcaacagca | cagacccagg | agtgttcaca | 1440 |
| gacctggcat | ctgtggacaa | ctcagagttt | cagcagctcc | tgaaccaggg | tgtgtccatg | 1500 |
| tctcactcca | cagctgagcc | catgctgatg | gagtaccctg | aagctataac | tcgcctggtg | 1560 |
| acagggtccc | agaggccccc | tgacccagct | cccacaccc | tggggacctc | ggggcttccc | 1620 |
| aatggtctct | ccggagatga | agacttctcc | tccattgcgg | acatggactt | ctctgctctt | 1680 |
| ttgagtcaga | tcagctcctg | ataa | | | | 1704 |

<210> SEQ ID NO 2

```
<211> LENGTH: 566
<212> TYPE: PRT
<213> ORGANISM: Artificial Sequence
<220> FEATURE:
<223> OTHER INFORMATION: Synthetic construct, Rel-A

<400> SEQUENCE: 2

Met Asp Trp Thr Trp Ile Leu Phe Leu Val Ala Ala Thr Arg Val
1               5                   10                  15

His Ser Asp Asp Leu Phe Pro Leu Ile Phe Pro Ser Glu Pro Ala Gln
            20                  25                  30

Ala Ser Gly Pro Tyr Val Glu Ile Ile Glu Gln Pro Lys Gln Arg Gly
        35                  40                  45

Met Arg Phe Arg Tyr Lys Cys Glu Gly Arg Ser Ala Gly Ser Ile Pro
    50                  55                  60

Gly Glu Arg Ser Thr Asp Thr Thr Lys Thr His Pro Thr Ile Lys Ile
65                  70                  75                  80

Asn Gly Tyr Thr Gly Pro Gly Thr Val Arg Ile Ser Leu Val Thr Lys
                85                  90                  95

Asp Pro Pro His Arg Pro His Pro His Glu Leu Val Gly Lys Asp Cys
            100                 105                 110

Arg Asp Gly Tyr Tyr Glu Ala Asp Leu Cys Pro Asp Arg Ser Ile His
        115                 120                 125

Ser Phe Gln Asn Leu Gly Ile Gln Cys Val Lys Lys Arg Asp Leu Glu
130                 135                 140

Gln Ala Ile Ser Gln Arg Ile Gln Thr Asn Asn Asn Pro Phe His Val
145                 150                 155                 160

Pro Ile Glu Glu Gln Arg Gly Asp Tyr Asp Leu Asn Ala Val Arg Leu
                165                 170                 175

Cys Phe Gln Val Thr Val Arg Asp Pro Ala Gly Arg Pro Leu Leu Leu
            180                 185                 190

Thr Pro Val Leu Ser His Pro Ile Phe Asp Asn Arg Ala Pro Asn Thr
        195                 200                 205

Ala Glu Leu Lys Ile Cys Arg Val Asn Arg Asn Ser Gly Ser Cys Leu
210                 215                 220

Gly Gly Asp Glu Ile Phe Leu Leu Cys Asp Lys Val Gln Lys Glu Asp
225                 230                 235                 240

Ile Glu Val Tyr Phe Thr Gly Pro Gly Trp Glu Ala Arg Gly Ser Phe
                245                 250                 255

Ser Gln Ala Asp Val His Arg Gln Val Ala Ile Val Phe Arg Thr Pro
            260                 265                 270

Pro Tyr Ala Asp Pro Ser Leu Gln Ala Pro Val Arg Val Ser Met Gln
        275                 280                 285

Leu Arg Arg Pro Ser Asp Arg Glu Leu Ser Glu Pro Met Glu Phe Gln
290                 295                 300

Tyr Leu Pro Asp Thr Asp Asp Arg His Arg Ile Glu Glu Lys Arg Lys
305                 310                 315                 320

Arg Thr Tyr Glu Thr Phe Lys Ser Ile Met Lys Lys Ser Pro Phe Asn
                325                 330                 335

Gly Pro Thr Glu Pro Arg Pro Pro Thr Arg Arg Ile Ala Val Pro Thr
            340                 345                 350

Arg Asn Ser Thr Ser Val Pro Lys Pro Ala Pro Gln Pro Tyr Thr Phe
        355                 360                 365

Pro Ala Ser Leu Ser Thr Ile Asn Phe Asp Glu Phe Ser Pro Met Leu
370                 375                 380
```

Leu Pro Ser Gly Gln Ile Ser Asn Gln Ala Leu Ala Leu Ala Pro Ser
385                 390                 395                 400

Ser Ala Pro Val Leu Ala Gln Thr Met Val Pro Ser Ser Ala Met Val
            405                 410                 415

Pro Leu Ala Gln Pro Pro Ala Pro Ala Pro Val Leu Thr Pro Gly Pro
        420                 425                 430

Pro Gln Ser Leu Ser Ala Pro Val Pro Lys Ser Thr Gln Ala Gly Glu
    435                 440                 445

Gly Thr Leu Ser Glu Ala Leu Leu His Leu Gln Phe Asp Ala Asp Glu
450                 455                 460

Asp Leu Gly Ala Leu Leu Gly Asn Ser Thr Asp Pro Gly Val Phe Thr
465                 470                 475                 480

Asp Leu Ala Ser Val Asp Asn Ser Glu Phe Gln Gln Leu Leu Asn Gln
            485                 490                 495

Gly Val Ser Met Ser His Ser Thr Ala Glu Pro Met Leu Met Glu Tyr
        500                 505                 510

Pro Glu Ala Ile Thr Arg Leu Val Thr Gly Ser Gln Arg Pro Pro Asp
    515                 520                 525

Pro Ala Pro Thr Pro Leu Gly Thr Ser Gly Leu Pro Asn Gly Leu Ser
530                 535                 540

Gly Asp Glu Asp Phe Ser Ser Ile Ala Asp Met Asp Phe Ser Ala Leu
545                 550                 555                 560

Leu Ser Gln Ile Ser Ser
                565

<210> SEQ ID NO 3
<211> LENGTH: 1647
<212> TYPE: DNA
<213> ORGANISM: Artificial Sequence
<220> FEATURE:
<223> OTHER INFORMATION: Synthetic construct, T-bet

<400> SEQUENCE: 3

```
atggattgga cttggatctt attttagtt gctgctgcta ctagagttca ttctgggatt      60
gtggaacctg gatgtggaga tatgctgact ggaacagaac ctatgccttc agatgagggg    120
agaggacccg gcgcagatca gcagcacaga ttcttttacc agagccagag cacaggac      180
cctactgata ggagagctgg cagctccctg gaaccccat acagcggagg agccctggtc     240
cctgcagctc cagggcgctt cctgggctcc tttgcttatc acccagggc caggtggct      300
ggatttcctg gaccagggga gttctttcca cccctgctg gagcagaagg gtacccaccc    360
gtggacggct atcccgctcc tgatccacga gcaggactgt accccgggcc tagggaggac    420
tatgcactgc cagccggcct ggaagtgtcc ggaaagctgc gggtcgccct gtccaaccac    480
ctgctgtggt ctaagttcaa tcagcatcag accgagatga tcattacaaa cagggcagg    540
aggatgttcc catttctgtc ttttactgtg gccggactgg aacccaccag tcactacagg    600
atgttcgtgg acgtggtcct ggtcgatcag caccattgga gatatcagtc cggaaagtgg    660
gtgcagtgcg gcaaagcaga gggatctatg ccaggaaacc gactgtacgt ccacccagat    720
agtcctaata caggcgctca ttggatgcgc aggaagtga gctttggaaa gctgaaactg    780
acaaacaata agggggcctc aaacaatgtg actcagatga tcgtcctgca gagcctgcac    840
aaatatcagc ccgcctgca tattgtggag gtcaacgacg agagcctga agcagcatgc    900
tccgcttcta tacccacgt gttcacattt caggagactc agttcatcgc tgtcacagca    960
```

-continued

```
taccagaacg ccgaaatcac tcagctgaag attgataaca atcctttcgc taaaggattt    1020
cgagagaatt tcgaatctat gtatgcaagt gtggacacta gcgtcccatc ccctccagga    1080
cctaactgtc agctgctggg gggcgatcca ttttcacccc tgctgagcaa tcagtaccca    1140
gtgcccagca ggttctatcc tgacctgcca gggcagccca aggatatgat ttctcagcca    1200
tactggctgg caccccccag agagcatagc tatgaggcag aatttcgggc cgtgagcatg    1260
aaaccaaccc tgctgccatc cgcccctgga ccaacagtgc cctactatag ggacaggac     1320 gtgctggcac ctggagctgg atggcctgtg caccacagt accccctaa gatgtctcct      1380 gcaggatggt tccgaccaat gcgcaccctg ccaatggacc ccggactggg ctctagtgag    1440
gaacagggat caagccctag tctgtggcca gaggtgacct cactgcagcc cgaacctagt    1500
gactcaggac tgggggaggg cgatacaaaa cgaaggagaa tcagcccata tccctcctct    1560
ggcgacagtt caagccccgc cggagcacca tccccatttg ataaggagac cgaaggccag    1620
ttctacaatt actttcccaa ctgataa                                         1647
```

<210> SEQ ID NO 4
<211> LENGTH: 547
<212> TYPE: PRT
<213> ORGANISM: Artificial Sequence
<220> FEATURE:
<223> OTHER INFORMATION: Synthetic construct, T-bet

<400> SEQUENCE: 4

```
Met Asp Trp Thr Trp Ile Leu Phe Leu Val Ala Ala Thr Arg Val
1               5                   10                  15

His Ser Gly Ile Val Glu Pro Gly Cys Gly Asp Met Leu Thr Gly Thr
            20                  25                  30

Glu Pro Met Pro Ser Asp Glu Gly Arg Gly Pro Gly Ala Asp Gln Gln
        35                  40                  45

His Arg Phe Phe Tyr Pro Glu Pro Gly Ala Gln Asp Pro Thr Asp Arg
    50                  55                  60

Arg Ala Gly Ser Ser Leu Gly Thr Pro Tyr Ser Gly Ala Leu Val
65                  70                  75                  80

Pro Ala Ala Pro Gly Arg Phe Leu Gly Ser Phe Ala Tyr Pro Pro Arg
                85                  90                  95

Ala Gln Val Ala Gly Phe Pro Gly Pro Gly Glu Phe Phe Pro Pro Pro
            100                 105                 110

Ala Gly Ala Glu Gly Tyr Pro Pro Val Asp Gly Tyr Pro Ala Pro Asp
        115                 120                 125

Pro Arg Ala Gly Leu Tyr Pro Gly Pro Arg Glu Asp Tyr Ala Leu Pro
    130                 135                 140

Ala Gly Leu Glu Val Ser Gly Lys Leu Arg Val Ala Leu Ser Asn His
145                 150                 155                 160

Leu Leu Trp Ser Lys Phe Asn Gln His Gln Thr Glu Met Ile Ile Thr
                165                 170                 175

Lys Gln Gly Arg Arg Met Phe Pro Phe Leu Ser Phe Thr Val Ala Gly
            180                 185                 190

Leu Glu Pro Thr Ser His Tyr Arg Met Phe Val Asp Val Val Leu Val
        195                 200                 205

Asp Gln His His Trp Arg Tyr Gln Ser Gly Lys Trp Val Gln Cys Gly
    210                 215                 220

Lys Ala Glu Gly Ser Met Pro Gly Asn Arg Leu Tyr Val His Pro Asp
225                 230                 235                 240
```

```
Ser Pro Asn Thr Gly Ala His Trp Met Arg Gln Glu Val Ser Phe Gly
                245                 250                 255

Lys Leu Lys Leu Thr Asn Asn Lys Gly Ala Ser Asn Asn Val Thr Gln
            260                 265                 270

Met Ile Val Leu Gln Ser Leu His Lys Tyr Gln Pro Arg Leu His Ile
        275                 280                 285

Val Glu Val Asn Asp Gly Glu Pro Glu Ala Ala Cys Ser Ala Ser Asn
    290                 295                 300

Thr His Val Phe Thr Phe Gln Glu Thr Gln Phe Ile Ala Val Thr Ala
305                 310                 315                 320

Tyr Gln Asn Ala Glu Ile Thr Gln Leu Lys Ile Asp Asn Asn Pro Phe
                325                 330                 335

Ala Lys Gly Phe Arg Glu Asn Phe Glu Ser Met Tyr Ala Ser Val Asp
            340                 345                 350

Thr Ser Val Pro Ser Pro Pro Gly Pro Asn Cys Gln Leu Leu Gly Gly
        355                 360                 365

Asp Pro Phe Ser Pro Leu Leu Ser Asn Gln Tyr Pro Val Pro Ser Arg
    370                 375                 380

Phe Tyr Pro Asp Leu Pro Gly Gln Pro Lys Asp Met Ile Ser Gln Pro
385                 390                 395                 400

Tyr Trp Leu Gly Thr Pro Arg Glu His Ser Tyr Glu Ala Glu Phe Arg
                405                 410                 415

Ala Val Ser Met Lys Pro Thr Leu Leu Pro Ser Ala Pro Gly Pro Thr
            420                 425                 430

Val Pro Tyr Tyr Arg Gly Gln Asp Val Leu Ala Pro Gly Ala Gly Trp
        435                 440                 445

Pro Val Ala Pro Gln Tyr Pro Pro Lys Met Ser Pro Ala Gly Trp Phe
    450                 455                 460

Arg Pro Met Arg Thr Leu Pro Met Asp Pro Gly Leu Gly Ser Ser Glu
465                 470                 475                 480

Glu Gln Gly Ser Ser Pro Ser Leu Trp Pro Glu Val Thr Ser Leu Gln
                485                 490                 495

Pro Glu Pro Ser Asp Ser Gly Leu Gly Glu Gly Asp Thr Lys Arg Arg
            500                 505                 510

Arg Ile Ser Pro Tyr Pro Ser Ser Gly Asp Ser Ser Ser Pro Ala Gly
        515                 520                 525

Ala Pro Ser Pro Phe Asp Lys Glu Thr Glu Gly Gln Phe Tyr Asn Tyr
    530                 535                 540

Phe Pro Asn
545

<210> SEQ ID NO 5
<211> LENGTH: 1881
<212> TYPE: DNA
<213> ORGANISM: Artificial Sequence
<220> FEATURE:
<223> OTHER INFORMATION: Synthetic construct, Eomes

<400> SEQUENCE: 5
atggattgga cttggatctt atttttagtt gctgctgcta ctagagttca ttctcttagt      60
gacaccgacg ccggggacgc atttgccagc gctgcggcag tggccaagcc ggggcccccg     120
gacggccgca agggctcccc ctgcggggag gaggagctgc cctccgccgc tgcagccgcc     180
gccgccgccg ccgccgcggc tgcggccact gcgcgctact ccatggacag cctgagctcc     240
gagcggtact acctccagtc ccccggtcct caggggtcgg agctggctgc ccctgctca      300
```

```
ctcttcccgt accaggcggc ggctggggcg ccccacggac ctgtgtaccc ggctcctaac    360
ggggcgcgct acccctacgg ctccatgctg ccccccggcg gcttcccgc ggctgtgtgc     420 ccacccggga gggcgcagtt cggcccagga gccggtgcgg gcagtggcgc gggcggtagc    480
agcggcgggg gcggcggccc gggcaccta t cagtacagcc aggggg ctcc gctctacggg  540 ccgtaccctg gagccgcagc ggcgggatct tgcggaggac tggggggcct ggggg ttcca   600 ggttctggct tccgtgccca cgtctacctg tgcaaccggc ctctgtggct caaattccac    660
cgccaccaaa ctgagatgat cattacgaaa cagggcaggc gcatgttt cc tttcttgagc   720 ttcaacataa acggactcaa tcccactgcc cactacaatg tgttcgtaga ggtggtgctg    780
gcggacccca ccactggcg cttccagggg ggcaaatggg tgacctgtgg caaagccgac     840
aataacatgc agggcaacaa aatgtatgtt cacccagagt ctcctaatac tggttcccac    900
tggatgagac aggagatttc attcgggaaa ttaaaactca ccaataacaa aggcgcaaat    960
aacaacaaca cccagatgat agtcttacaa tccttacaca ataccaacc ccgactgcat    1020 attgttgaag ttacagagga tggcgtggag gacttgaatg agccctcaaa gacccagact   1080
tttaccttct cagaaacgca attcattgca gtgactgcct accaaaacac cgatattact    1140
caactaaaga ttgatcataa ccccttcgca aaaggcttca gagacaacta tgattcatcc    1200
catcagattg tccctggagg tcggtacggc gttcaatcct tcttcccgga gccctttgtc    1260
aacactttac ctcaagcccg ctattataat ggcgagagaa ccgtgccaca gaccaacggc    1320
ctcctttcac cccaacagag cgaagaggtg gccaaccctc cccagcggtg gcttgtcacg    1380
cctgtccagc aacctgggac caacaaacta gacatcagtt cctatgaatc tgaatatact    1440
tctagcacat tgctcccata tggcattaaa tccttgcccc ttcagacatc ccatgccctg    1500
gggtattacc cagacccaac cttttcctgca atggcagggt ggggaggtcg aggttcttac    1560
cagaggaaga tggcagctgg actaccatgg acctccagaa caagcccacc tgtgttctct    1620
gaagatcagc tctccaagga gaaagtgaaa gaggaaattg gctcttcttg gatagagaca    1680
cccccttcca tcaaatctct agattccaat gattcaggag tatacaccag tgcttgtaag    1740
cgaaggcggc tgtctcctag caactccagt aatgaaaatt caccctccat aaagtgtgag    1800
gacattaatg ctgaagagta tagtaaagac acctcaaaag gcatgggagg gtattatgct    1860
ttttacacaa ctccctgata a                                              1881
```

<210> SEQ ID NO 6  
<211> LENGTH: 625  
<212> TYPE: PRT  
<213> ORGANISM: Artificial Sequence  
<220> FEATURE:  
<223> OTHER INFORMATION: Synthetic construct, Eomes

<400> SEQUENCE: 6

```
Met Asp Trp Thr Trp Ile Leu Phe Leu Val Ala Ala Thr Arg Val
1               5                   10                  15

His Ser Leu Ser Asp Thr Asp Ala Gly Asp Ala Phe Ala Ser Ala Ala
            20                  25                  30

Ala Val Ala Lys Pro Gly Pro Pro Asp Gly Arg Lys Gly Ser Pro Cys
        35                  40                  45

Gly Glu Glu Glu Leu Pro Ser Ala Ala Ala Ala Ala Ala Ala Ala Ala
    50                  55                  60

Ala Ala Ala Ala Ala Thr Ala Arg Tyr Ser Met Asp Ser Leu Ser Ser
65                  70                  75                  80
```

-continued

Glu Arg Tyr Tyr Leu Gln Ser Pro Gly Pro Gln Gly Ser Glu Leu Ala
                 85                  90                  95

Ala Pro Cys Ser Leu Phe Pro Tyr Gln Ala Ala Gly Ala Pro His
            100                 105                 110

Gly Pro Val Tyr Pro Ala Pro Asn Gly Ala Arg Tyr Pro Tyr Gly Ser
            115                 120                 125

Met Leu Pro Pro Gly Gly Phe Pro Ala Ala Val Cys Pro Pro Gly Arg
130                 135                 140

Ala Gln Phe Gly Pro Gly Ala Gly Ala Gly Ser Gly Ala Gly Gly Ser
145                 150                 155                 160

Ser Gly Gly Gly Gly Pro Gly Thr Tyr Gln Tyr Ser Gln Gly Ala
                165                 170                 175

Pro Leu Tyr Gly Pro Tyr Pro Gly Ala Ala Ala Gly Ser Cys Gly
                180                 185                 190

Gly Leu Gly Gly Leu Gly Val Pro Gly Ser Gly Phe Arg Ala His Val
        195                 200                 205

Tyr Leu Cys Asn Arg Pro Leu Trp Leu Lys Phe His Arg His Gln Thr
        210                 215                 220

Glu Met Ile Ile Thr Lys Gln Gly Arg Arg Met Phe Pro Phe Leu Ser
225                 230                 235                 240

Phe Asn Ile Asn Gly Leu Asn Pro Thr Ala His Tyr Asn Val Phe Val
                245                 250                 255

Glu Val Val Leu Ala Asp Pro Asn His Trp Arg Phe Gln Gly Gly Lys
                260                 265                 270

Trp Val Thr Cys Gly Lys Ala Asp Asn Asn Met Gln Gly Asn Lys Met
                275                 280                 285

Tyr Val His Pro Glu Ser Pro Asn Thr Gly Ser His Trp Met Arg Gln
        290                 295                 300

Glu Ile Ser Phe Gly Lys Leu Lys Leu Thr Asn Asn Lys Gly Ala Asn
305                 310                 315                 320

Asn Asn Asn Thr Gln Met Ile Val Leu Gln Ser Leu His Lys Tyr Gln
                325                 330                 335

Pro Arg Leu His Ile Val Glu Val Thr Glu Asp Gly Val Glu Asp Leu
                340                 345                 350

Asn Glu Pro Ser Lys Thr Gln Thr Phe Thr Phe Ser Glu Thr Gln Phe
                355                 360                 365

Ile Ala Val Thr Ala Tyr Gln Asn Thr Asp Ile Thr Gln Leu Lys Ile
                370                 375                 380

Asp His Asn Pro Phe Ala Lys Gly Phe Arg Asp Asn Tyr Asp Ser Ser
385                 390                 395                 400

His Gln Ile Val Pro Gly Gly Arg Tyr Gly Val Gln Ser Phe Phe Pro
                405                 410                 415

Glu Pro Phe Val Asn Thr Leu Pro Gln Ala Arg Tyr Tyr Asn Gly Glu
                420                 425                 430

Arg Thr Val Pro Gln Thr Asn Gly Leu Leu Ser Pro Gln Gln Ser Glu
            435                 440                 445

Glu Val Ala Asn Pro Pro Gln Arg Trp Leu Val Thr Pro Val Gln Gln
        450                 455                 460

Pro Gly Thr Asn Lys Leu Asp Ile Ser Ser Tyr Glu Ser Glu Tyr Thr
465                 470                 475                 480

Ser Ser Thr Leu Leu Pro Tyr Gly Ile Lys Ser Leu Pro Leu Gln Thr
                485                 490                 495

```
Ser His Ala Leu Gly Tyr Tyr Pro Asp Pro Thr Phe Pro Ala Met Ala
            500                 505                 510

Gly Trp Gly Gly Arg Gly Ser Tyr Gln Arg Lys Met Ala Ala Gly Leu
        515                 520                 525

Pro Trp Thr Ser Arg Thr Ser Pro Thr Val Phe Ser Glu Asp Gln Leu
        530                 535                 540

Ser Lys Glu Lys Val Lys Glu Ile Gly Ser Ser Trp Ile Glu Thr
545                 550                 555                 560

Pro Pro Ser Ile Lys Ser Leu Asp Ser Asn Asp Ser Gly Val Tyr Thr
                565                 570                 575

Ser Ala Cys Lys Arg Arg Arg Leu Ser Pro Ser Asn Ser Ser Asn Glu
            580                 585                 590

Asn Ser Pro Ser Ile Lys Cys Glu Asp Ile Asn Ala Glu Glu Tyr Ser
                595                 600                 605

Lys Asp Thr Ser Lys Gly Met Gly Gly Tyr Tyr Ala Phe Tyr Thr Thr
            610                 615                 620

Pro
625

<210> SEQ ID NO 7
<211> LENGTH: 753
<212> TYPE: DNA
<213> ORGANISM: Artificial Sequence
<220> FEATURE:
<223> OTHER INFORMATION: Synthetic construct, FLT3L

<400> SEQUENCE: 7
atggattgga cttggatctt atttttagtt gctgctgcta ctagagttca ttctacggtc       60 ctcgccctg cgtggtcgcc caactcgtca ctgctgttgc tccttctgtt gttgtcaccc      120
tgtttgcgag ggacaccgga ctgttatttc agccatagcc ccatctcgtc caacttcaaa     180
gtaaagtttc gggaactcac tgaccacctt ctcaaagatt accccgtcac agtggcggtg    240
aatcttcaag acgaaaagca ctgtaaggcc ctctggagcc tgtttctggc acagagatgg    300
atcgagcaac ttaaaacggt cgcgggttca agatgcaga ccctcttgga agatgtgaat     360
acagagattc actttgtcac gtcatgcacc tttcagcctc tgcccgaatg cctcagattc    420
gtacaaacta atatctccca tctcctcaag gacacatgca cccagttgct cgcgttgaag    480
ccgtgcatcg ggaaagcatg tcagaacttc tcccgctgcc ttgaggtaca gtgccagccc    540
gattcctcga cgcttcttcc cccgagatcg cctattgcct tggaggccac ggagctgccc    600
gaacctcgac cgcgccagtt gctgctcctc ctgttgctct tgcttccgct tacactcgtg    660
ctgctggctg cagcgtgggg attgaggtgg cagagggcta ggcggagagg cgagctgcat    720
ccgggagtgc cattgccgtc gcacccatga taa                                 753

<210> SEQ ID NO 8
<211> LENGTH: 249
<212> TYPE: PRT
<213> ORGANISM: Artificial Sequence
<220> FEATURE:
<223> OTHER INFORMATION: Synthetic construct, FLT3L

<400> SEQUENCE: 8

Met Asp Trp Thr Trp Ile Leu Phe Leu Val Ala Ala Thr Arg Val
1               5                   10                  15

His Ser Thr Val Leu Ala Pro Ala Trp Ser Pro Asn Ser Ser Leu Leu
            20                  25                  30
```

| | | | | | | | | | | | | | |
|---|---|---|---|---|---|---|---|---|---|---|---|---|---|
|Leu|Leu|Leu|Leu|Leu|Leu|Ser|Pro|Cys|Leu|Arg|Gly|Thr|Pro|Asp|Cys|
| | |35| | | |40| | | |45| | | | |

Tyr Phe Ser His Ser Pro Ile Ser Ser Asn Phe Lys Val Lys Phe Arg
 50                  55                  60

Glu Leu Thr Asp His Leu Leu Lys Asp Tyr Pro Val Thr Val Ala Val
65                  70                  75                  80

Asn Leu Gln Asp Glu Lys His Cys Lys Ala Leu Trp Ser Leu Phe Leu
                85                  90                  95

Ala Gln Arg Trp Ile Glu Gln Leu Lys Thr Val Ala Gly Ser Lys Met
            100                 105                 110

Gln Thr Leu Leu Glu Asp Val Asn Thr Glu Ile His Phe Val Thr Ser
        115                 120                 125

Cys Thr Phe Gln Pro Leu Pro Glu Cys Leu Arg Phe Val Gln Thr Asn
    130                 135                 140

Ile Ser His Leu Leu Lys Asp Thr Cys Thr Gln Leu Leu Ala Leu Lys
145                 150                 155                 160

Pro Cys Ile Gly Lys Ala Cys Gln Asn Phe Ser Arg Cys Leu Glu Val
                165                 170                 175

Gln Cys Gln Pro Asp Ser Ser Thr Leu Leu Pro Pro Arg Ser Pro Ile
            180                 185                 190

Ala Leu Glu Ala Thr Glu Leu Pro Glu Pro Arg Pro Arg Gln Leu Leu
        195                 200                 205

Leu Leu Leu Leu Leu Leu Pro Leu Thr Leu Val Leu Leu Ala Ala
    210                 215                 220

Ala Trp Gly Leu Arg Trp Gln Arg Ala Arg Arg Gly Glu Leu His
225                 230                 235                 240

Pro Gly Val Pro Leu Pro Ser His Pro
                245

<210> SEQ ID NO 9
<211> LENGTH: 803
<212> TYPE: DNA
<213> ORGANISM: Artificial Sequence
<220> FEATURE:
<223> OTHER INFORMATION: Synthetic construct, TWEAK

<400> SEQUENCE: 9

```
atggattgga cttggatctt attttagtt gctgctgcta ctagagttca ttctgccgca      60
agacggagtc agcgaagacg gggaagaagg ggagaacctg gcaccgcact gctggcacct     120
ctggtcctga gctgggact ggctctggca tgcctgggc tgctgctggt ggtcgtgtct       180
ctgggcagtt gggcaactct gtcagcccag gagccaagcc aggaggaact gaccgccgaa     240
gacaggagag agccccctga actgaaccct cagaccgagg aatcccagga tgtcgtgcca     300
ttcctggagc agctggtccg accacggcgc tctgccccaa agggacgaaa agctcgaccc     360
cgaagggcaa tcgccgctca ctacgaggtg catccacgac caggacagga cggagcacag     420
gctggagtcg atggcaccgt gagcggatgg gaggaaacaa agattaacag ctcctctcct     480
ctgagatatg acagacagat cggcgagttc acagtgatta gagcaggact gtactatctg     540
tactgtcagg tccactttga cgaaggaaag gccgtgtacc tgaaactggt ctgctggtca     600
atggggtgct ggccctgcga tgcctggagg agttcagcgc acagcagcc agttcacctg      660
gaccacagct gcgactgtgc caggtgtctg gactgctgcc actgcgacct gggagctccc     720
tgagaatccg gactctgccc tgggctcatc tgaaggctgc tccatttctg acatactttg     780
ggctgttcca ggtccactaa tga                                              803
```

<210> SEQ ID NO 10
<211> LENGTH: 240
<212> TYPE: PRT
<213> ORGANISM: Artificial Sequence
<220> FEATURE:
<223> OTHER INFORMATION: Synthetic construct, TWEAK

<400> SEQUENCE: 10

```
Met Asp Trp Thr Trp Ile Leu Phe Leu Val Ala Ala Thr Arg Val
1               5                   10                  15

His Ser Ala Ala Arg Arg Ser Gln Arg Arg Gly Arg Arg Gly Glu
                20                  25                  30

Pro Gly Thr Ala Leu Leu Ala Pro Leu Val Leu Ser Leu Gly Leu Ala
                35                  40                  45

Leu Ala Cys Leu Gly Leu Leu Leu Val Val Ser Leu Gly Ser Trp
            50                  55                  60

Ala Thr Leu Ser Ala Gln Glu Pro Ser Gln Glu Leu Thr Ala Glu
65                  70                  75                  80

Asp Arg Arg Glu Pro Pro Glu Leu Asn Pro Gln Thr Glu Glu Ser Gln
                85                  90                  95

Asp Val Val Pro Phe Leu Glu Gln Leu Val Arg Pro Arg Arg Ser Ala
                100                 105                 110

Pro Lys Gly Arg Lys Ala Arg Pro Arg Arg Ala Ile Ala Ala His Tyr
                115                 120                 125

Glu Val His Pro Arg Pro Gly Gln Asp Gly Ala Gln Ala Gly Val Asp
                130                 135                 140

Gly Thr Val Ser Gly Trp Glu Glu Thr Lys Ile Asn Ser Ser Ser Pro
145                 150                 155                 160

Leu Arg Tyr Asp Arg Gln Ile Gly Glu Phe Thr Val Ile Arg Ala Gly
                165                 170                 175

Leu Tyr Tyr Leu Tyr Cys Gln Val His Phe Asp Glu Gly Lys Ala Val
                180                 185                 190

Tyr Leu Lys Leu Val Cys Trp Ser Met Gly Cys Trp Pro Cys Asp Ala
                195                 200                 205

Trp Arg Ser Ser Ala Pro Gln Gln Pro Val His Leu Asp His Ser Cys
                210                 215                 220

Asp Cys Ala Arg Cys Leu Asp Cys Cys His Cys Asp Leu Gly Ala Pro
225                 230                 235                 240
```

<210> SEQ ID NO 11
<211> LENGTH: 576
<212> TYPE: DNA
<213> ORGANISM: Artificial Sequence
<220> FEATURE:
<223> OTHER INFORMATION: Synthetic construct, GITRL

<400> SEQUENCE: 11

```
atggattgga cttggatctt attttttagtt gctgctgcta ctagagttca ttctgaagaa      60 atgccccctga gagaatcaag tccccagaga gctgagaggt gtaagaagtc ctggctgctg    120
tgcatcgtcg ccctgctgct gatgctgctg tgcagtctgg aactctgat ctacacctca      180 ctgaaaccta cagccattga gagctgtatg gtgaagttcg aactgagctc ctctaaatgg    240
cacatgacta gtcccaagcc tcattgcgtg aacaccacat ccgacgggaa gctgaaaatc    300
ctgcagtctg ggacctacct gatctatggc caggtcatcc cagtcgacaa gaaatacatc    360
aaggataatg ccccccttcgt ggtccagatc tacaagaaaa acgacgtgct gcagacactg    420
```

```
atgaatgatt ttcagatcct gcccattggc ggagtctacg agctgcacgc tggcgacaac      480
atctatctga gtttaattc caaggatcat attcagaaaa caaacaccta ttgggggatt      540
atcctgatgc cagacctgcc cttcattagc taatga                                576
```

<210> SEQ ID NO 12
<211> LENGTH: 190
<212> TYPE: PRT
<213> ORGANISM: Artificial Sequence
<220> FEATURE:
<223> OTHER INFORMATION: Synthetic construct, GITRL

<400> SEQUENCE: 12

```
Met Asp Trp Thr Trp Ile Leu Phe Leu Val Ala Ala Thr Arg Val
1               5                   10                  15

His Ser Glu Glu Met Pro Leu Arg Glu Ser Pro Gln Arg Ala Glu
                20                  25                  30

Arg Cys Lys Lys Ser Trp Leu Leu Cys Ile Val Ala Leu Leu Leu Met
35                  40                  45

Leu Leu Cys Ser Leu Gly Thr Leu Ile Tyr Thr Ser Leu Lys Pro Thr
50                  55                  60

Ala Ile Glu Ser Cys Met Val Lys Phe Glu Leu Ser Ser Ser Lys Trp
65                  70                  75                  80

His Met Thr Ser Pro Lys Pro His Cys Val Asn Thr Thr Ser Asp Gly
                85                  90                  95

Lys Leu Lys Ile Leu Gln Ser Gly Thr Tyr Leu Ile Tyr Gly Gln Val
                100                 105                 110

Ile Pro Val Asp Lys Lys Tyr Ile Lys Asp Asn Ala Pro Phe Val Val
                115                 120                 125

Gln Ile Tyr Lys Lys Asn Asp Val Leu Gln Thr Leu Met Asn Asp Phe
                130                 135                 140

Gln Ile Leu Pro Ile Gly Gly Val Tyr Glu Leu His Ala Gly Asp Asn
145                 150                 155                 160

Ile Tyr Leu Lys Phe Asn Ser Lys Asp His Ile Gln Lys Thr Asn Thr
                165                 170                 175

Tyr Trp Gly Ile Ile Leu Met Pro Asp Leu Pro Phe Ile Ser
                180                 185                 190
```

<210> SEQ ID NO 13
<211> LENGTH: 1209
<212> TYPE: DNA
<213> ORGANISM: Artificial Sequence
<220> FEATURE:
<223> OTHER INFORMATION: Synthetic construct, STING

<400> SEQUENCE: 13

```
ggatccgcca ccatggactg gacctggatt ctgttcctgg tcgccgctgc cacccgcgtg      60
cattcacctt actcaaacct gcaccctgcc attccccgac cagaggacac ccggtcaaag     120
tacgtggctc tgatcttcct ggtcgcaagc ctgatgattc tgtgggtggc taaggaccct     180
cccaaccata ccctgaaata tctggctctg cacctggcat cccatgagct ggggctgctg     240
ctgaagaatc tgtgctgtct ggccgaggaa ctgtgccacg tgcagagtag gtaccaggga     300
tcatattgga aagcagtcag agcctgcctg ggtgtcccta tccattgtat ggcaatgatt     360
ctgctgagct cctacttcta tttctgcag aacaccgccg atatctacct gtcctggatg     420
ttcggcctgc tggtgctgta taagtctctg agtatgctgc tgggactgca gagcctgaca     480
```

```
cctgccgagg tgtccgctgt ctgcgaggaa aagaaactga acgtggcaca cggactggcc    540
tggtcttact atatcgggta cctgcggctg attctgccag gcctgcaggc tcggattcgc    600
atgtttaatc agctgcataa caatatgctg tccggcgcag gatctaggag actgtatatc    660
ctgttcccac tggactgcgg ggtgcccgat aacctgtctg tggtcgaccc taatattagg    720
ttcagggata tgctgccaca gcagaacatc gaccgagccg gcattaagaa ccgcgtgtac    780
tcaaatagcg tctatgagat cctggaaaat gggcagcccg caggcgtgtg cattctggag    840
tacgccaccc ctctgcagac actgttcgct atgtctcagg acgccaaggc tggcttcagc    900
agggaggatc gactgaaaca ggccaaactg ttctgccgca cactggagga aatcctggag    960
gacgtgccag aaagtcggaa caattgtcgc ctgattgtct accaggagcc cactgatggc   1020
aactcctttt ctctgagtca ggaagtgctg aggcacatca gacaggagga aaaagaggaa   1080
gtcactatga atgcaccaat gaccagcgtg gctccacccc cttcagtcct gagccaggaa   1140
ccacgcctgc tgattagcgg aatggaccag ccactgccac tgcgaactga cctgatttga   1200
taactcgag                                                           1209
```

<210> SEQ ID NO 14
<211> LENGTH: 395
<212> TYPE: PRT
<213> ORGANISM: Artificial Sequence
<220> FEATURE:
<223> OTHER INFORMATION: Synthetic construct, STING

<400> SEQUENCE: 14

```
Met Asp Trp Thr Trp Ile Leu Phe Leu Val Ala Ala Thr Arg Val
1               5                  10                  15

His Ser Pro Tyr Ser Asn Leu His Pro Ala Ile Pro Arg Pro Arg Gly
            20                  25                  30

His Arg Ser Lys Tyr Val Ala Leu Ile Phe Leu Val Ala Ser Leu Met
        35                  40                  45

Ile Leu Trp Val Ala Lys Asp Pro Pro Asn His Thr Leu Lys Tyr Leu
    50                  55                  60

Ala Leu His Leu Ala Ser His Glu Leu Gly Leu Leu Leu Lys Asn Leu
65                  70                  75                  80

Cys Cys Leu Ala Glu Glu Leu Cys His Val Gln Ser Arg Tyr Gln Gly
                85                  90                  95

Ser Tyr Trp Lys Ala Val Arg Ala Cys Leu Gly Cys Pro Ile His Cys
            100                 105                 110

Met Ala Met Ile Leu Leu Ser Ser Tyr Phe Tyr Phe Leu Gln Asn Thr
        115                 120                 125

Ala Asp Ile Tyr Leu Ser Trp Met Phe Gly Leu Leu Val Leu Tyr Lys
    130                 135                 140

Ser Leu Ser Met Leu Leu Gly Leu Gln Ser Leu Thr Pro Ala Glu Val
145                 150                 155                 160

Ser Ala Val Cys Glu Glu Lys Lys Leu Asn Val Ala His Gly Leu Ala
                165                 170                 175

Trp Ser Tyr Tyr Ile Gly Tyr Leu Arg Leu Ile Leu Pro Gly Leu Gln
            180                 185                 190

Ala Arg Ile Arg Met Phe Asn Gln Leu His Asn Asn Met Leu Ser Gly
        195                 200                 205

Ala Gly Ser Arg Arg Leu Tyr Ile Leu Phe Pro Leu Asp Cys Gly Val
    210                 215                 220

Pro Asp Asn Leu Ser Val Val Asp Pro Asn Ile Arg Phe Arg Asp Met
```

-continued

```
                225                 230                 235                 240

Leu Pro Gln Gln Asn Ile Asp Arg Ala Gly Ile Lys Asn Arg Val Tyr
                    245                 250                 255

Ser Asn Ser Val Tyr Glu Ile Leu Glu Asn Gly Gln Pro Ala Gly Val
                    260                 265                 270

Cys Ile Leu Glu Tyr Ala Thr Pro Leu Gln Thr Leu Phe Ala Met Ser
                275                 280                 285

Gln Asp Ala Lys Ala Gly Phe Ser Arg Glu Asp Arg Leu Glu Gln Ala
            290                 295                 300

Lys Leu Phe Cys Arg Thr Leu Glu Glu Ile Leu Glu Asp Val Pro Glu
305                 310                 315                 320

Ser Arg Asn Asn Cys Arg Leu Ile Val Tyr Gln Glu Pro Thr Asp Gly
                    325                 330                 335

Asn Ser Phe Ser Leu Ser Gln Glu Val Leu Arg His Ile Arg Gln Glu
                340                 345                 350

Glu Lys Glu Glu Val Thr Met Asn Ala Pro Met Thr Ser Val Ala Pro
                355                 360                 365

Pro Pro Ser Val Leu Ser Gln Glu Pro Arg Leu Leu Ile Ser Gly Met
        370                 375                 380

Asp Gln Pro Leu Pro Leu Arg Thr Asp Leu Ile
385                 390                 395
```